United States Patent
Kusleika et al.

(10) Patent No.: US 9,962,274 B2
(45) Date of Patent: May 8, 2018

(54) STRETCHABLE STENT AND DELIVERY

(75) Inventors: Rich Kusleika, Eden Prairie, MN (US);
Doug Duchon, Chanhassen, MN (US);
Joe Tatalovich, St. Louis Park, MN (US)

(73) Assignee: Covidien LP, Mansfield, MA (US)

( * ) Notice: Subject to any disclaimer, the term of this patent is extended or adjusted under 35 U.S.C. 154(b) by 855 days.

(21) Appl. No.: 13/548,428

(22) Filed: Jul. 13, 2012

(65) Prior Publication Data
US 2013/0006348 A1    Jan. 3, 2013

Related U.S. Application Data

(62) Division of application No. 12/099,544, filed on Apr. 8, 2008, now Pat. No. 8,241,344.

(Continued)

(51) Int. Cl.
*A61F 2/06* (2013.01)
*A61F 2/95* (2013.01)
(Continued)

(52) U.S. Cl.
CPC ............. *A61F 2/95* (2013.01); *A61F 2/91* (2013.01); *A61F 2/915* (2013.01); *A61F 2002/91525* (2013.01); *A61F 2002/91533* (2013.01); *A61F 2002/91558* (2013.01); *A61F 2002/9517* (2013.01); *A61F 2210/0057* (2013.01); *A61F 2220/005* (2013.01); *A61F 2220/0058* (2013.01); *A61F 2230/0054* (2013.01)

(58) Field of Classification Search
USPC ............ 623/1.15, 1.16, 1.18, 1.19, 1.2, 1.21
See application file for complete search history.

(56) References Cited

U.S. PATENT DOCUMENTS

| 4,655,771 A | 4/1987 | Wallsten |
| 5,476,508 A | 12/1995 | Amstrup |

(Continued)

FOREIGN PATENT DOCUMENTS

| EP | 1304092 | 4/2003 |
| EP | 1441668 | 5/2003 |

(Continued)

OTHER PUBLICATIONS

International Search Report of related application No. PCT/US2008/059665 mailed Jul. 17, 2008.

(Continued)

*Primary Examiner* — Jonathan Miles

(57) ABSTRACT

An implant delivery catheter enables permanent modification of the implant length in the vicinity of the treatment site prior to radial expansion thereof. The implant is releasable carried between inner and outer tubular members of the delivery catheter which, upon repositioning relative to one another using an actuator mechanism, impart any of tensile, compressile or torquing forces to the implant causing permanent modification of the implant length. In one embodiment, the circumference of the implant is substantially similar both before and after modification of the implant length. In another embodiment, the implant includes a plurality of strut sections interconnected by bridges which are capable of the deformation along the longitudinal axis of the implant.

26 Claims, 17 Drawing Sheets

Related U.S. Application Data

(60) Provisional application No. 60/910,690, filed on Apr. 9, 2007.

(51) Int. Cl.
  *A61F 2/91* (2013.01)
  *A61F 2/915* (2013.01)

(56) References Cited

U.S. PATENT DOCUMENTS

| | | | |
|---|---|---|---|
| 5,755,781 A * | 5/1998 | Jayaraman | 623/1.16 |
| 5,849,037 A | 12/1998 | Frid | |
| 6,102,942 A | 8/2000 | Ahari | |
| 6,129,756 A | 10/2000 | Kugler et al. | |
| 6,193,744 B1 * | 2/2001 | Ehr | 623/1.16 |
| 6,241,762 B1 * | 6/2001 | Shanley | 623/1.17 |
| 6,540,773 B2 | 4/2003 | Dong | |
| 6,554,855 B1 | 4/2003 | Dong | |
| 6,773,456 B1 | 8/2004 | Gordon et al. | |
| 6,893,457 B2 | 5/2005 | Dong | |
| 6,929,663 B2 | 8/2005 | Rioux et al. | |
| 6,939,372 B2 | 9/2005 | Dong | |
| 6,976,955 B2 | 12/2005 | Hardin et al. | |
| 7,029,492 B1 | 4/2006 | Mitsudou et al. | |
| 2001/0029397 A1 | 10/2001 | Thompson | |
| 2002/0072793 A1 | 6/2002 | Rolando et al. | |
| 2003/0055480 A1 | 3/2003 | Fischell et al. | |
| 2003/0204241 A1 | 10/2003 | Dong | |
| 2004/0087975 A1 | 5/2004 | Lucatero et al. | |
| 2004/0122506 A1 * | 6/2004 | Shanley et al. | 623/1.16 |
| 2004/0193283 A1 | 9/2004 | Rioux et al. | |
| 2005/0043778 A1 | 2/2005 | Von Oepen et al. | |
| 2005/0149159 A1 | 7/2005 | Andreas et al. | |
| 2005/0267566 A1 | 12/2005 | Rioux et al. | |
| 2006/0229700 A1 | 10/2006 | Acosta et al. | |
| 2006/0259120 A1 | 11/2006 | Vongphakdy et al. | |
| 2007/0032857 A1 * | 2/2007 | Schmid et al. | 623/1.16 |

FOREIGN PATENT DOCUMENTS

| | | |
|---|---|---|
| EP | 1605889 | 10/2004 |
| EP | 1328212 | 1/2007 |
| JP | 2001276230 | 10/2001 |
| WO | WO9850102 | 11/1998 |
| WO | WO2004/087016 | 10/2004 |

OTHER PUBLICATIONS

Extended Search Report from counterpart European Application No. 15175451.2, dated Nov. 16, 2015, 7 pp.

* cited by examiner

FIG. 7A  FIG. 7B ated from the delivery catheter at the modified length. The implant radially expands to a deployed position once released from the delivery catheter. The modification of the implant can include, for example, permanent stretching such that the pre-deployed length is increased to an adjusted pre-deployed length. The ability to adjust the pre-deployed length in a permanent manner in the vicinity of the treatment site reduces the likelihood that multiple stents will be needed to treat the entire length of the diseased vessel. The ability of the physician to adjust the pre-deployed length at the time of delivery within a patient can simplify the stenting procedure and reduce the number and size of stents that need to be maintained in inventory. In some cases, the number of stents used in a procedure can be reduced to a single stent in situations that would have otherwise required multiple stents.

STRETCHABLE STENT AND DELIVERY

CROSS REFERENCE TO RELATED APPLICATIONS

This application is a divisional application of U.S. patent application Ser. No. 12/099,544 filed on Apr. 8, 2008 which claims the benefit of U.S. Provisional Application Ser. No. 60/910,690 filed on Apr. 9, 2007, each of which are incorporated herein by reference in its entirety.

FIELD OF THE DISCLOSURE

The present disclosure relates to an implant and a system for delivering the implant to a site in a body lumen. More particularly, this disclosure pertains to a vascular implant such as a stent.

BACKGROUND OF THE DISCLOSURE

Stents are widely used for supporting a lumen structure in a patient's body. For example, stents may be used to maintain patency of a coronary artery, carotid artery, cerebral artery, other blood vessels including veins, or other body lumens such as the ureter, urethra, bronchus, esophagus, or other passage.

Stents are commonly metallic tubular structures made from stainless steel, Nitinol, Elgiloy, cobalt chrome alloys, tantalum, and other metals, although polymer stents are known. Stents can be permanent enduring implants, or can be bioabsorbable at least in part. Bioabsorbable stents can be polymeric, bio-polymeric, ceramic, bio-ceramic, or metallic, and may elute over time substances such as drugs. Non-bioabsorbable stents may also release drugs over time. Stents are passed through a body lumen in a collapsed state. At the point of an obstruction or other deployment site in the body lumen, the stent is expanded to an expanded diameter to support the lumen at the deployment site.

In certain designs, stents are open-celled tubes that are expanded by inflatable balloons at the deployment site. This type of stent is often referred to as a "balloon expandable" stent. Stent delivery systems for balloon expandable stents are typically comprised of an inflatable balloon mounted on a two lumen tube. The stent delivery system with stent compressed thereon can be advanced to a treatment site over a guidewire, and the balloon inflated to expand and deploy the stent.

Other stents are so-called "self expanding" stents and do not use balloons to cause the expansion of the stent. An example of a self-expanding stent is a tube (e.g., a coil tube or an open-celled tube) made of an elastically deformable material (e.g., a superelastic material such a nitinol). This type of stent is secured to a stent delivery device under tension in a collapsed state. At the deployment site, the stent is released so that internal tension within the stent causes the stent to self-expand to its enlarged diameter.

Other self-expanding stents are made of so-called shape-memory metals. Such shape-memory stents experience a phase change at the elevated temperature of the human body. The phase change results in expansion from a collapsed state to an enlarged state.

A very popular type of self expanding stent is an open-celled tube made from self-expanding nitinol, for example, the Protégé GPS stent from ev3, Inc. of Plymouth, Minn. Open cell tube stents are commonly made by laser cutting of tubes, or cutting patterns into sheets followed by or preceded by welding the sheet into a tube shape, and other methods.

Another delivery technique for a self expanding stent is to mount the collapsed stent on a distal end of a stent delivery system. Such a system can be comprised of an outer tubular member and an inner tubular member. The inner and outer tubular members are axially slideable relative to one another. The stent (in the collapsed state) is mounted surrounding the inner tubular member at its distal end. The outer tubular member (also called the outer sheath) surrounds the stent at the distal end.

Prior to advancing the stent delivery system through the body lumen, a guide wire is first passed through the body lumen to the deployment site. The inner tube of the delivery system is hollow throughout at least a portion of its length such that it can be advanced over the guide wire to the deployment site. The combined structure (i.e., stent mounted on stent delivery system) is passed through the patient's lumen until the distal end of the delivery system arrives at the deployment site within the body lumen. The delivery system and/or the stent may include radiopaque markers to permit a physician to visualize stent positioning under fluoroscopy prior to deployment. At the deployment site, the outer sheath is retracted to expose the stent. The exposed stent is free to self-expand within the body lumen. Following expansion of the stent, the inner tube is free to pass through the stent such that the delivery system can be removed through the body lumen leaving the stent in place at the deployment site.

It can be difficult to estimate the length of the diseased portion of a vessel and therefore the stent length needed for treatment of the disease. This is particularly true for long diseased segments, segments that are tortuous, and segments that are oriented at angles to the plane of the imaging modality used (due to image foreshortening). If the stent chosen for treatment is too long then un-diseased vessel will be treated, and if the stent chosen is too short then diseased vessel will be untreated. Both of these scenarios are undesirable. In some cases physicians will treat a portion of the length of the diseased vessel with a first stent and will implant a second stent to treat the remainder of the length of the diseased vessel, overlapping the two stents to assure that no portion of the diseased vessel is left untreated. This approach is also undesirable because problems such as corrosion between dissimilar metals, excessive vessel stiffening, stent fracture, and reduced stent fatigue life can arise at the site of overlap. Problems secondary to stent fracture can include pain, bleeding, vessel occlusion, vessel perforation, high restenosis rate, non-uniform drug delivery profile, non-even vessel coverage and other problems. Re-intervention may be required to resolve these problems. Further, use of multiple stents to cover a treatment site increases procedural time and cost.

Some have attempted to improve the precision with which to estimate the needed implant length. For example, a guidewire having visualizable markers separated by a known distance can be inserted into the treatment region. However, these techniques have not become widespread in part because marker wires do not perform as well as the specialty guidewires preferred by physicians.

What is needed is an implant and associated delivery system that permits delivery and deployment of stents that are well matched to the length of diseased segments.

SUMMARY OF THE DISCLOSURE

An implant delivery catheter enables permanent modification of the implant length in the vicinity of the treatment site prior to radial expansion thereof. The implant is releasable carried between inner and outer tubular members of the delivery catheter which, upon repositioning relative to one another using an actuator mechanism, impart any of tensile, compressile or torquing forces to the implant causing permanent modification of the implant length. In one embodiment, the circumference of the implant is substantially similar both before and after modification of the implant length. In another embodiment, the implant includes a plurality of strut sections interconnected by bridges which are capable of the deformation along the longitudinal axis of the implant.

According to one aspect of the disclosure, an implant for insertion into a body lumen comprises a plurality of cells at least partially defined by a plurality of struts and a plurality of bridges, selected of the cells disposed at proximal and distal ends of the implant and having terminal ends attached thereto The implant has an initial length L1 extending along a longitudinal axis and an initial circumference C1 extending circumferencially about the longitudinal axis, wherein the implant assumes a deformation circumference C2 having a value within 0% to 10% of a value of the initial circumference C1 following application of a deformation force to the terminal ends thereof.

According to a second aspect of the disclosure, a medical device comprises a tubular implant having first and second ends and extending for an initial length L1 along a longitudinal axis and an implant delivery system. The implant delivery system comprises a catheter having an outer tubular member disposed about an inner tubular member, the first end of the implant operatively secured to the outer tubular member and the second end of the implant operatively secured to the inner tubular member; and an actuator mechanism movably coupled to one of the outer tubular member and the inner tubular member for changing relative positions of the outer tubular member and the inner tubular member along a second axis substantially parallel with the longitudinal axis; wherein changes in the relative positions of the outer tubular member and the inner tubular member change the initial length L1 of the implant to a modified length L2.

According to a third aspect of the disclosure, a method for placement of an implant within a body lumen comprises: A) providing an implant having a generally tubular shaped body defining a number of cells and extending for an initial continuous length L1 along an axis; B) advancing the implant with a delivery catheter to a site within the body lumen; C) modifying the length L1 to a second continuous length L2 along the axis with the delivery catheter prior to deployment at the site within the body lumen, the number of cells defined by the tubular shaped body being the same for both length L1 and length L2; and D) initiating radial expansion of the implant about the axis at the site within the body lumen.

According to a fourth aspect of the invention, implant for insertion into a body lumen comprises a tubular body extending for an initial length L1 along a longitudinal axis and having and initial circumference C1 about the longitudinal axis. The tubular body further comprises plurality of strut structures and a plurality bridge structures collectively defining a plurality of cells, selected of the plurality of cells being disposed at proximal and distal ends of the tubular body and having terminal ends attached thereto. One of the plurality of strut structures and bridge structures are capable of deformation in a direction tending toward the longitudinal axis of the tubular body when a force, parallel to the longitudinal axis, is applied to the end terminals.

BRIEF DESCRIPTION OF THE DRAWINGS

The above and further advantages of the inventive concept may be better understood by referring to the following description in conjunction with the accompanying drawings in which:

FIGS. 7A, 7B and 7C illustrate enlarged views of the distal portion of the system of FIG. 5A in various states of implant deployment;

DETAILED DESCRIPTION

With reference now to the various drawing figures a description is provided of embodiments that are examples of how inventive aspects in accordance with the principles of the present disclosure may be practiced. It is to be understood that both the foregoing general description and the following detailed description are exemplary and explanatory only and are not restrictive of the broad inventive aspects disclosed herein. It will also be appreciated that while the inventive concepts disclosed herein are often described using stents as exemplary implants these inventive concepts are not limited to stents or to the particular stent configurations disclosed herein, but are instead applicable to any number of different implant configurations.

In this specification various drawing figures and descriptions are provided of embodiments that are examples of stretchable implants, that is, implants that can be lengthened from a shorter length to a longer length, generally by applying a tensile force to the ends of the implant. It is contemplated that the implants described in the examples can also be used as shortenable implants, that is, implants that can be compressed from a longer length to a shorter length by applying a compressile force to the ends of the implant. It is further contemplated that the implant delivery catheters, systems, and methods described for use with stretchable implants are equally useful when applied to shortenable implants.

Figure 1A:
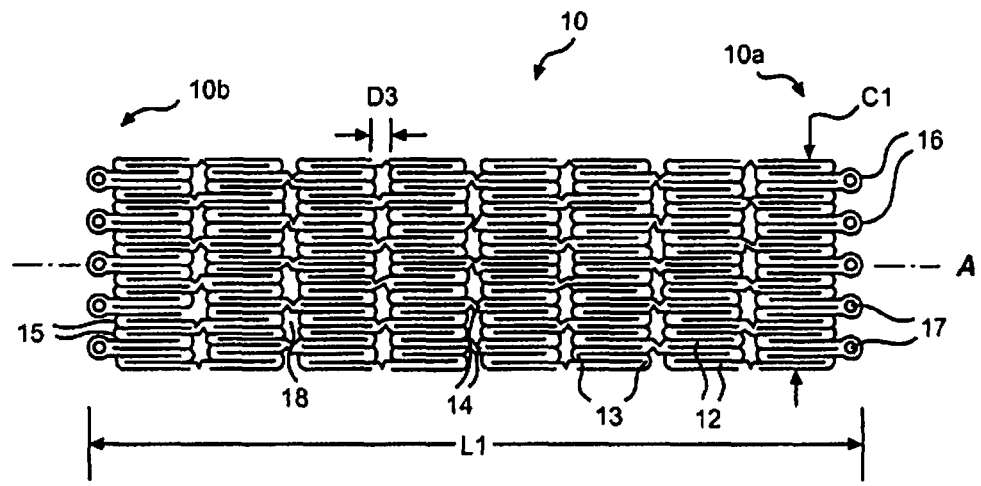
FIGS. 1A and 1B illustrate plan views of an exemplary stretchable implant embodiment having structure that interlocks with structure of a stretchable implant delivery catheter. The implant is shown contracted and un-stretched in FIG. 1A and contracted and stretched in FIG. 1B. The implant and interlock structures are shown cut longitudinally and laid flat.
Figure 1B:
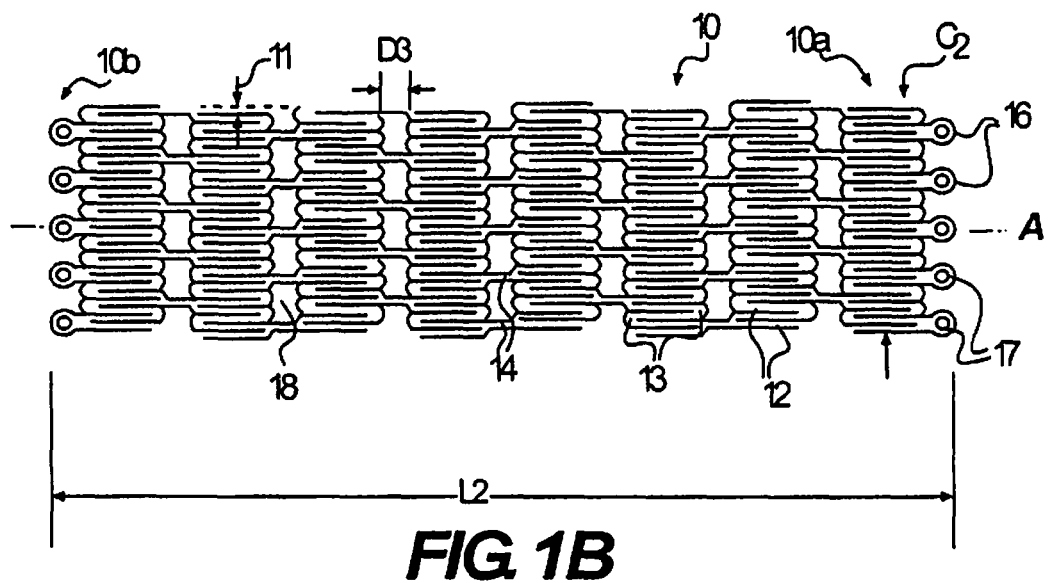

FIGS. 1A and 1B illustrate stretchable implant 10 comprised of struts 12, bridges 14, and one or more tab 16 at each end 10b, 10a of implant 10. The implant is shown cut longitudinally and laid flat. While eight rows of struts are illustrated in FIGS. 1A and 1B it is understood that any number greater than two rows of struts are suitable for the disclosure. Similarly, while fifteen struts per row are illustrated in FIGS. 1A and 1B it is understood that any number greater than three struts per row are suitable for the disclosure. The perimeters enclosed by struts and bridges define cells 18. Struts are joined at bend regions 13. In some embodiments tabs 16 are comprised of holes therethrough having markers 17 attached to tabs. Tabs 16 interlock with retainers of stretchable implant delivery catheter (discussed below). Implant 10 can be stretched along axis A by stretchable implant delivery catheter (also discussed below).

Implant 10 has length L and circumference C, and includes a plurality of struts 12. At least some of the struts 12 have bend regions 13 without tabs 16, or free terminal ends 15 that define proximal and distal ends 10a and 10b of implant 10. Implant 10 includes interlock geometry in the form of tabs 16 attached to or integral to one or more free terminal ends 15 of struts 12. The tabs 16 project outwardly from the struts 12 in a circumferential direction (i.e. in a direction coinciding with the circumference C of the implant 10). Markers 17 are located adjacent the proximal or distal ends 10a, 10b or both of implant 10 and may be located at any position along the length of the stent between the proximal and distal stent ends 10a, 10b. Markers 17 can be attached to implant 10 by techniques such as adhesives, heat fusion, interference fit, fasteners, intermediate members, as coatings, or by other techniques. In one embodiment, markers 17 are comprised of radiopaque materials press fit into a through-hole provided in tab 16. In one embodiment, shown in FIGS. 1A and 1B, the tabs are circular enlargements. It will be appreciated that other shapes and other interlock configurations could also be used. Suitable designs of tabs 16 and markers 17 include but are not limited to those described in FIGS. 6A, 6B, 7 to 13, 14A, 14B, 15A and 15B and related discussions thereof in U.S. Pat. No. 6,623,518 entitled "Implant Delivery System with Interlock", and include but are not limited to those described in FIGS. 4 to 15 and related discussions thereof in U.S. Pat. No. 6,814,746 entitled "Implant Delivery System with Marker Interlock", the contents of which being incorporated in their entirety herein by reference for all purposes.

In other embodiments markers 17 are comprised of ultrasonic markers, MRI safe markers, or other markers. In one embodiment ultrasonic markers 17 permit a physician to accurately determine the position of implant 10 within a patient under ultrasonic visualization. Ultrasonic visualization is especially useful for visualizing implant 10 during non-invasive follow-up and monitoring. Materials for ultrasonic marker 17 have an acoustical density sufficiently different from implant 10 to provide suitable visualization via ultrasonic techniques. Exemplary materials comprise polymers (for metallic stents), metals such as tantalum, platinum, gold, tungsten and alloys of such metals (for polymeric or ceramic stents), hollow glass spheres or microspheres, and other materials.

In another embodiment MRI safe markers permit a physician to accurately determine the position of implant 10 within a patient under magnetic resonance imaging. MRI visualization is especially useful for visualizing implant 10 during non-invasive follow-up and monitoring. Exemplary materials for making MRI safe marker 17 have a magnetic signature sufficiently different from implant 10 to provide suitable visualization via MRI techniques. Exemplary materials comprise polymers (for metallic stents), metals such as tantalum, platinum, gold, tungsten and alloys of such metals (for polymeric or ceramic stents), non-ferrous materials, and other materials.

Implant 10 may be comprised of metal, polymer, ceramic, permanent enduring materials, and may comprise either of or both of non-bioabsorbable and bioabsorbable materials. Exemplary materials include but are not limited to Nitinol, stainless steel, cobalt chromium alloys, Elgiloy, magnesium alloys, polylactic acid, poly glycolic acid, poly ester amide (PEA), poly ester urethane (PEU), amino acid based bioanalogous polymers, tungsten, tantalum, platinum, polymers, bio-polymers, ceramics, bio-ceramics, or metallic glasses. Part or all of implant 10 may elute over time substances such as drugs, biologics, gene therapies, anti-thrombotics, coagulants, anti-inflammatory drugs, immunomodulator drugs, anti-proliferatives, migration inhibitors, extracellular matrix modulators, healing promoters, re-endothelialization promoters, or other materials. In one embodiment, implant 10 is comprised of shape memory urethane polymer. Implant 10 can be manufactured by forming cells 18 through the wall of the tube, by means such as laser cutting, electrochemical etching, grinding, piercing, or other means. In some embodiments implant 10 is formed by electroforming. In one embodiment, implant 10 can be manufactured by cutting (e.g., laser cutting) the various features from a solid tube of superelastic Nitinol metal. In some embodiments implant 10 is finished by processes to remove slag (such as microgrit blasting), to remove implant material having a heat affected zone or other imperfections (e.g. by electropolishing), and to render surface of implant 10 more resistant to corrosion (e.g. by surface passivation).

In other embodiments implant 10 may be comprised of intertwined, joined, or non-woven filaments. In some embodiments filaments are braided, woven, knitted, circular knitted, compressed, or otherwise fabricated into a porous mesh structure having cells 18. Filaments may be joined at one or more filament crossings by sintering, bonding, soldering, fusing, welding, or other means.

Implant 10 may have one or more of the following characteristics: self expanding, self contracting, balloon expandable, and shape memory. In one embodiment implant 10 is comprised of balloon expandable stainless steel alloy. In another embodiment implant 10 is comprised of superelastic nitinol struts 12 and non-superelastic malleable bridges 14. In various embodiments implant 10 is a stent, a stent graft, a mesh covered stent, or other implants.

Implant 10 has un-stretched length L1 as illustrated in FIG. 1A and stretched length L2 as illustrated in FIG. 1B. In the examples of FIGS. 1A and 1B bridges 14 can be lengthened along axis A in response to tensile force applied to ends 10a, 10b of implant 10. Lengthening of implant 10 causes bridges 14 to align in a direction more parallel with stent axis A, thereby increasing distance D3 between free terminal ends and causing a small offset 11 between adjacent rows of struts 12. Lengthening of contracted implant 10 causes little or no change in stretched circumference C2 as compared to un-stretched circumference C1. In some embodiments lengthened implants remain lengthened after removal of the tensile forces which caused the implant to lengthen. Implants are envisioned which can be lengthened any incremental amount up to the maximum stretched length of the implant. Implants having a maximum stretched length L2 from 3% to 50% greater than the implant un-stretched length L1 are contemplated. In one embodiment, implant 10 has a maximum stretched length 5% greater than the implant un-stretched length. In other embodiments, implant 10 has a maximum stretched length 10%, 15%, 20%, 25%, 30%, 35%, 40%, or 45% greater than the implant un-stretched length. Implants having a stretched circumference C2 within 0% to 10% of un-stretched circumference C1 are contemplated. In one embodiment, implant 10 has a maximum stretched circumference within 9% of the implant un-stretched circumference. In other embodiments, implant 10 has a maximum stretched circumference within 1%, 2%, 3%, 4%, 5%, 6%, 7%, or 8% of the implant un-stretched circumference.

Figure 3A:
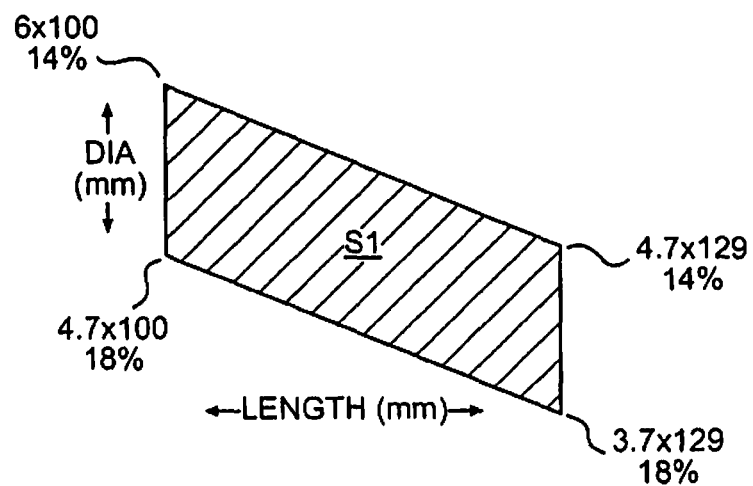
FIGS. 3A, 3B, 4A, and 4B illustrate characteristics of exemplary stretchable implants.

In some embodiments of stretchable implants, for example a metallic arterial stent, it is desirable to have the percentage of vessel inner wall area that is covered by the expanded metal stent ("percent metal coverage") to fall within a pre-programmed range. In one example a 6 mm diameter by 100 mm long (6×100) stent is designed to be lengthened only by a maximum of 29%, to have a pre-programmed average percent metal coverage of 14% at the nominal size of 6×100 and to have a percent metal coverage of 14-18% over its indicated usable range. As illustrated in FIG. 3A, the exemplary stent, deployed at 100 mm long in a 6 mm vessel, has 14% metal coverage. The exemplary stent, deployed at 100 mm long in a 4.7 mm vessel, has 18% metal coverage ((14%/18%)*6 mm=4.7 mm). The exemplary stent, deployed at 129 mm long in a 4.7 mm vessel, has 14% metal coverage ((18%/14%)*100 mm=129 mm) and deployed at 129 mm long in a 3.7 mm vessel, has 18% metal coverage ((14%/18%)*4.7 mm=3.7 mm). The shaded region S1 in FIG. 3A describes the indicated usable range of this exemplary stent when stretched. Stents deployed in vessels having a length and diameter combination within shaded region S1 will have percent metal coverage of 14-18%.

Figure 3B:
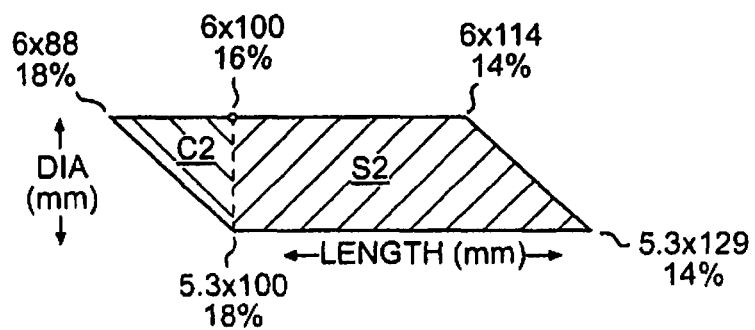

In another example a 6 mm diameter by 100 mm long (6×100) stent is designed to be deployed in vessels having a limited diameter range (6 mm to 5.3 mm), be mainly stretchable but to a limited extent contractable, to have a pre-programmed average percent metal coverage of 14% at the nominal size of 6×100, and to have a percent metal coverage of 14-18% over it's indicated usable range. As illustrated in FIG. 3B, the exemplary stent, deployed at 100 mm long in a 6 mm vessel, has 16% metal coverage. The exemplary stent, deployed at 114 mm long in a 6 mm vessel, has 18% metal coverage, and deployed at 88 mm long in a 6 mm vessel, has 14% metal coverage. The exemplary stent, deployed at 100 mm long in a 5.3 mm vessel, has 18% metal coverage and deployed at 129 mm long in a 5.3 mm vessel, has 14% metal coverage. The shaded region S2 in FIG. 3B describes the indicated usable range of this exemplary stent when stretched and the shaded region C2 in FIG. 3B describes the indicated usable range of this exemplary stent when contracted. Stents deployed in vessels having a length and diameter combination within shaded regions S2 and C2 will have percent metal coverage of 14-18%.

Figure 4A:
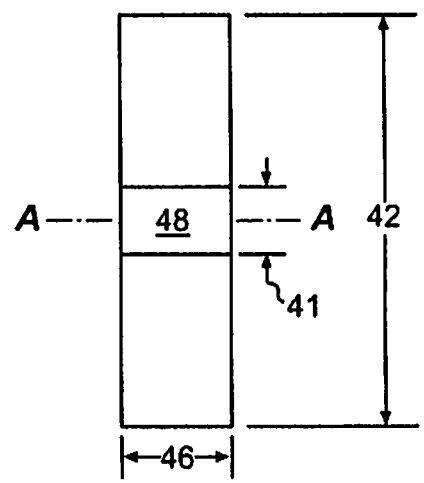
Figure 4B:
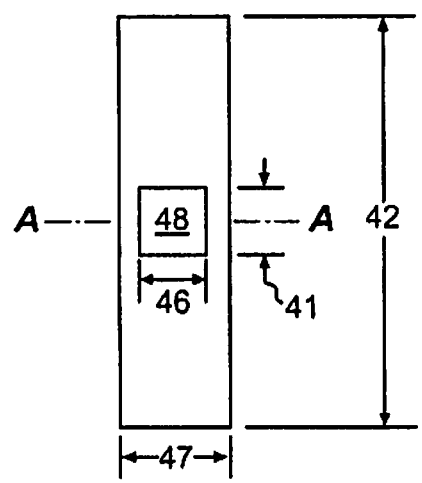

In other embodiments of stretchable implants it is desirable for a plurality of repeating units, such as a cell 18, to have similar or the same axial and radial expansion or contraction characteristics, or both. In one embodiment the implant has similar axial and radial cellular expansion characteristics so that the implant will uniformly stretch and will uniformly expand. In FIGS. 4A and 4B, cell 18 of implant 10 is represented by cell 48. Cell 48 is shown unexpanded, cut longitudinally and laid flat. In one embodiment of implant 10, when the implant is expanded, representative cell 48 will expand from length 41 to length 42 with little or no change to axial dimension 46 (FIG. 4A). In another embodiment (FIG. 4B), when implant 10 is first stretched and then expanded, representative cell 48 will first stretch from axial dimension 46 to axial dimension 47 with little or no change to length 41, and will then expand from length 41 to length 42 with little or no change to axial dimension 47. Ratio's of expanded cell length 42 to unexpanded cell length 41 of from 200% to 800% are contemplated. In one embodiment, implant 10 has a ratio of expanded cell length to unexpanded cell length of 300%. In other embodiments, implant 10 has a ratio of expanded cell length to unexpanded cell length of 350%, 400%, 450%, 500%, 550%, 600%, 675%, or 750%. Ratio's of stretched cell axial dimension 47 to unstretched cell axial dimension 46 of from 3% to 50% are contemplated. In one embodiment, implant 10 has a ratio of stretched cell axial dimension to unstretched cell axial dimension of 5%. In other embodiments, implant has a ratio of stretched cell axial dimension to unstretched cell axial dimension of 10%, 15%, 20%, 25%, 30%, 35%, 40%, or 45%.

Figure 2A:
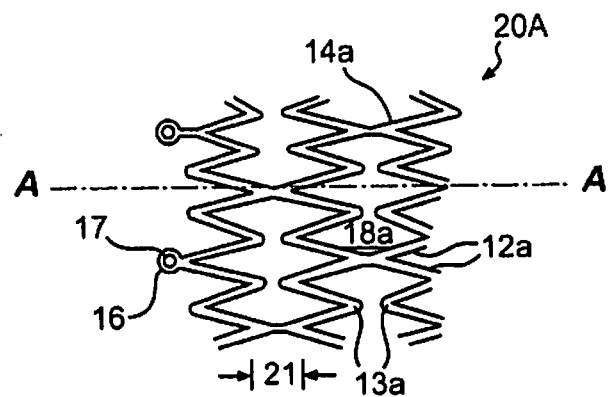
FIGS. 2A, 2B, 2C, 2D, 2E and 2F illustrate plan views of portions of exemplary stretchable implants.

FIGS. 2A to 2E illustrate alternate embodiments of stretchable implants. FIG. 2A illustrates stretchable implant 20A comprised of struts 12a, bridges 14a, and one or more tabs 16 having markers 17. The implant is shown partially expanded, cut longitudinally and laid flat. The perimeter of struts and bridges define cells 18a. Struts are joined at bend regions 13a. Implant 20A has substantially the same construction, dimensions, and function as implant 10 described above in conjunction with FIGS. 1A, 1B, 3A, 3B, 4A, and 4B. Implant 20A can be stretched along axis A by stretchable implant delivery catheter (discussed below). In one embodiment cross sectional area of bridges 14a normal to axis A is less than cross sectional area of struts 12a normal to axis A and less than cross sectional area of tabs 16 normal to axis A. In one embodiment bridges are locally thinned using processes such as electroetching with or without use of masks, grinding, polishing, laser ablation, or other processes. In another embodiment strut thickness is selectively increased by stiffening a particular region by means of an additive process such as plating, electrodeposition, sputtering, coating, or other processes. In another embodiment yield force of bridges 14a normal to axis A is less than yield force of struts 12a normal to axis A and less than yield force of tabs 16 normal to axis A. In a further embodiment cross sectional area of bridges 14a normal to axis A is less than cross sectional area of struts 12a normal to axis A and less than cross sectional area of tabs 16 normal to axis A and yield force of bridges 14a normal to axis A is less than yield force of struts 12a normal to axis A and less than yield force of tabs 16 normal to axis A. In some embodiments one or more bridge 14a is comprised of malleable material such as annealed metal, engineering polymer, or other materials. Annealed metal may be produced by selectively heating bridges 14a using processes such as laser heating, electrical resistive heating, inductive heating, or other processes.

In use, when tension is applied to implant 20A bridges 14a lengthen in the direction of axis A (i.e. dimension 21 increases) but struts 12a and tabs 16 do not lengthen in the direction of axis A. In some embodiments bridges 14a are permanently deformed by the applied tensile forces. After implant lengthening the implant is radially expanded. In one embodiment implant 20A is a self expanding stent and the stent is allowed to self-expand by means of sheath removal. In another embodiment implant 20A is a balloon expandable stent and the stent is expanded by means of balloon inflation. During implant 20A stretching and expansion implant dimensional changes fall within the ranges disclosed for implant 10 (above).

Figure 2B:
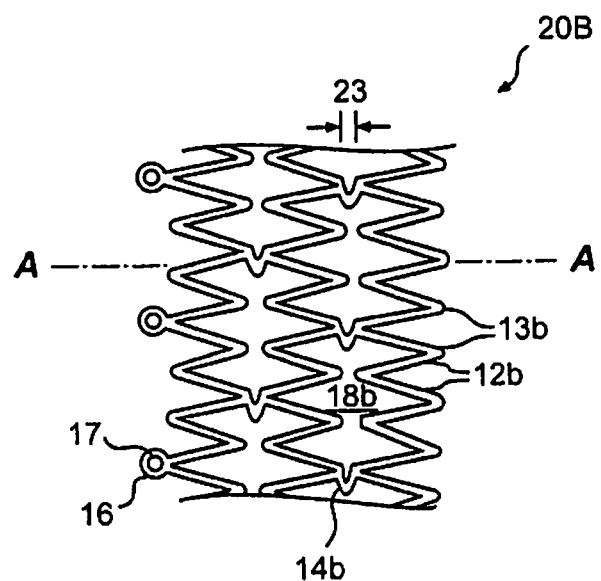
Figure 2C:
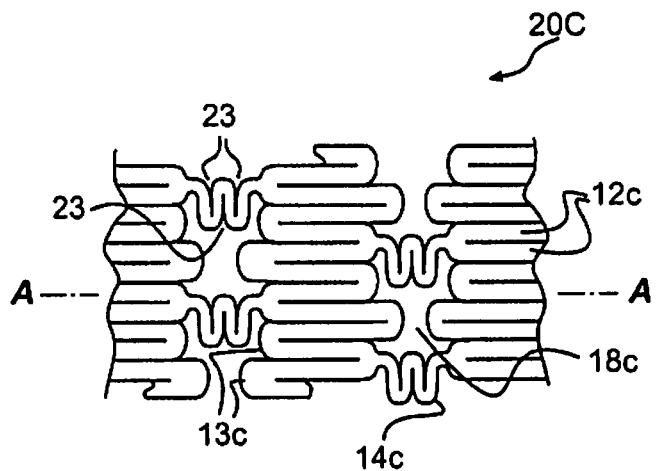

FIGS. 2B and 2C illustrate stretchable implants 20B, 20C comprised of struts 12b, 12c, bridges 14b, 14c, and one or more tabs 16 having markers 17. The implants are shown partially expanded, cut longitudinally and laid flat. The perimeter of struts and bridges define cells 18b, 18c. Struts are joined at bend regions 13b, 13c. Implant 20A has substantially the same construction, dimensions, and function as implant 10 described above in conjunction with FIGS. 1A, 1B, 3A, 3B, 4A, and 4B. Implants 20B and 20C can be stretched along axis A by stretchable implant delivery catheter (discussed below). Bridges 14b, 14c are comprised of a serpentine shape and one or more gap 23. The perimeter of struts and bridges define cells 18b, 18c. Struts are joined at bend regions 13b, 13c. FIG. 2B illustrates stretchable implant 20B comprised of bridges 14b having one gap 23 and FIG. 2C illustrates stretchable implant 20C comprised of bridges 14c having three gaps 23. In other embodiments bridges can have serpentine shapes with any number of bends and lengths along circular perimeter of stent. Bridges can also join one or more bend regions radially adjacent to each other or can join one or more bend regions radially offset from each other. In some embodiments one or more bridge 14b, 14c is comprised of malleable material such as annealed metal, engineering polymer, or other material. In one embodiment yield force of bridges 14b, 14c normal to axis A is less than yield force of struts 12b, 12c normal to axis A and less than yield force of tabs 16 normal to axis A. In some embodiments one or more bridge 14b, 14c is comprised of malleable material such as annealed metal, produced by selectively heating bridges 14a using processes such as laser heating, electrical resistive heating, inductive heating, or other processes. In another embodiment bridges are locally thinned using processes such as electroetching with or without use of masks, chemical milling, EDM, grinding, polishing, laser ablation, or other processes.

In use, when tension is applied to implant 20B, 20C gap(s) 23 in bridges 14b, 14c widen in the direction of axis A but struts 12b, 12c and tabs 16 do not elongate in direction of axis A. In some embodiments bridges 14b, 14c are permanently deformed by the applied tensile forces. After implant lengthening the implant is radially expanded. In one embodiment implant 20B, 20C is a self expanding stent and the stent is allowed to self-expand by means of sheath removal. In another embodiment implant 20B, 20C is a balloon expandable stent and the stent is expanded by means of balloon inflation. During implant 20B, 20C stretching and expansion implant dimensional changes fall within the ranges disclosed for implant 10 (above).

Figure 2D:
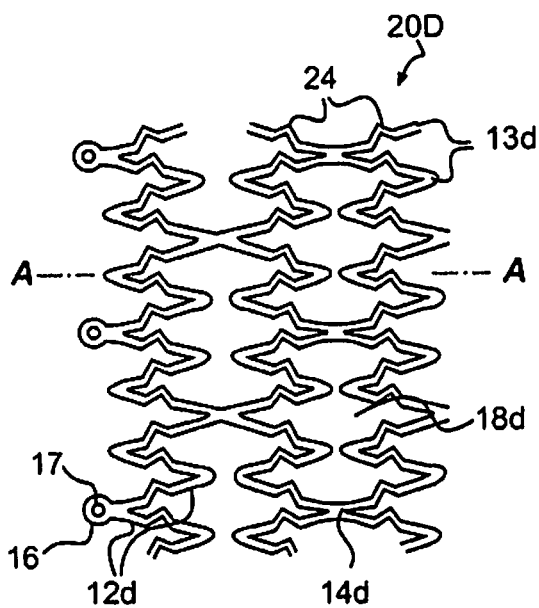
Figure 2E:
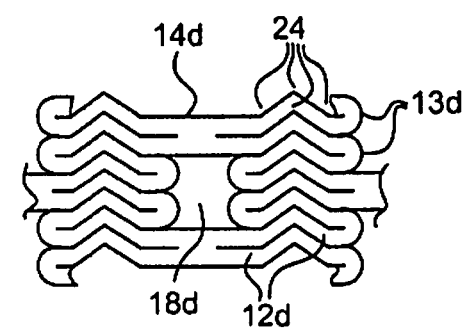

FIGS. 2D and 2E illustrate stretchable implant 20D comprised of struts 12d, bridges 14d, and one or more tabs 16 having markers 17. The implant is shown cut longitudinally and laid flat, also the implant is shown partially expanded in FIG. 2D and contracted to a delivery configuration in FIG. 2E. The perimeter of struts and bridges define cells 18d. Struts are joined at bend regions 13d and follow a serpentine path along their length with one or more bend regions 24 along the length of each strut. Implant 20D has substantially the same construction, dimensions, and function as implant 10 described above in conjunction with FIGS. 1A, 1B, 3A, 3B, 4A, and 4B. Implant 20D can be stretched along axis A by stretchable implant delivery catheter (discussed below). In some embodiments one or more bend region 24 is comprised of malleable material such as annealed metal. In one embodiment yield force of bend region 24 normal to axis A is less than yield force of struts 12d normal to axis A and less than yield force of tabs 16 normal to axis A. In some embodiments one or more bend region 24 is comprised of malleable material such as annealed metal, produced by selectively heating bend region 24 using processes such as laser heating, electrical resistive heating, inductive heating, or other processes. In another embodiment bend points are locally thinned using processes such as electroetching with or without use of masks, grinding, polishing, laser ablation, or other processes.

In use, when tension is applied to implant 20D struts 12d straighten and lengthen in the direction of axis A due to deformation in bend regions 24. Tabs 16 do not lengthen when tension is applied. In some embodiments bend regions 24 are permanently deformed by the applied tensile forces. After implant lengthening the implant is radially expanded. In one embodiment implant 20D is a self expanding stent and the stent is allowed to self-expand by means of sheath removal. In another embodiment implant 20D is a balloon expandable stent and the stent is expanded by means of balloon inflation. During implant 20D stretching and expansion implant dimensional changes fall within the ranges disclosed for implant 10 (above).

Figure 2F:
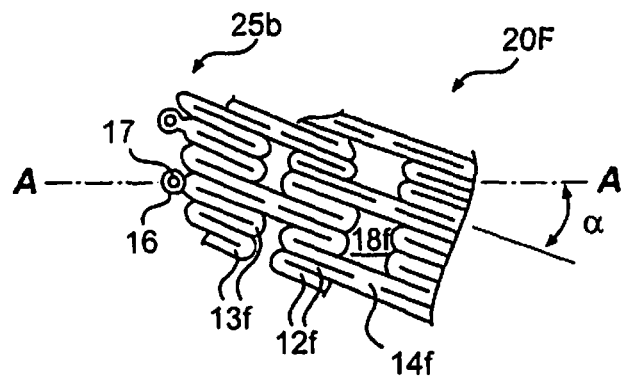
Figure 2G:
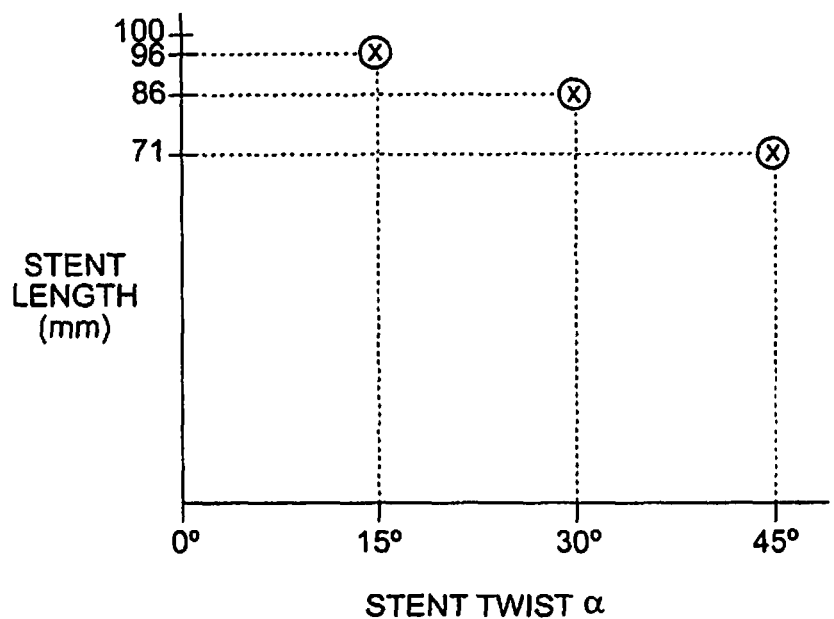
FIG. 2G is a graph illustrating certain characteristics of exemplary stretchable implant portion illustrated in FIG. 2F.

FIG. 2F illustrates a portion of stretchable implant 20F comprised of struts 12f, bridges 14f, proximal end 25a (not shown), distal end 25b, and one or more tabs 16 having markers 17. The implant is shown contracted to a delivery configuration, cut longitudinally and laid flat. The perimeter of struts and bridges define cells 18f. Struts are joined at bend regions 13f, are malleable at least in part, and are oriented at twist angle α relative to axis A. Implant 20F has substantially the same construction, dimensions, and function as implant 10 described above in conjunction with FIGS. 1A, 1B, 3A, 3B, 4A, and 4B. In one embodiment torsional yield force of struts 12f and bridges 14f is less than torsional yield force of tabs 16. In some embodiments one or more strut 12f and bridge 14f is comprised of malleable material such as annealed metal, produced by selectively heating strut 12f and/or bridge 14f using processes such as laser heating, electrical resistive heating, inductive heating, or other processes. In another embodiment struts 12f and/or bridges 14f are locally thinned using processes such as electroetching with or without use of masks, grinding, polishing, laser ablation, or other processes. Implant 20F can be lengthened along axis A by stretchable implant delivery catheter (discussed below) by twisting proximal end 25a (not shown) relative to distal end 25b in a direction that reduces twist angle α. In one embodiment, a stent having a length of 71 mm when α=45° can be lengthened by any incremental amount by twisting proximal end 25a (not shown) relative to distal end 25b in a direction that reduces twist angle α, to a maximum length when α=0°. For one embodiment where implant 20F is a 100 mm long stent when fully stretched, FIG. 2G illustrates stent length vs. stent twist angle.

In use, when proximal end 25a (not shown) of implant 20F is twisted relative to distal end 25b of implant in a direction that reduces twist angle α, struts 12f become oriented in a direction more parallel to axis A, thereby lengthening the implant the direction of axis A. In some embodiments malleable struts 12f and bend regions 13f are permanently deformed by the applied torsional forces. After implant lengthening the implant is radially expanded. In one embodiment implant 20F is a self expanding stent and the stent is allowed to self-expand by means of sheath removal. In another embodiment implant 20F is a balloon expandable stent and the stent is expanded by means of balloon inflation. During implant 20F stretching and expansion implant dimensional changes fall within the ranges disclosed for implant 10 (above).

In some embodiments the implant when stretched will lengthen preferentially in certain regions along the length of the implant. For example, implants 10, 20A, 20B and 20C tend to lengthen in the region adjacent to bridges 14, 14a, 14b and 14c respectively. When expanded, implants 10, 20A, 20B and 20C will have a structure that may be characterized as a series of linearly separated serpentine rings interconnected by axial bridges. In one example deployed implants 10, 20A, 20B and 20C are stretched more in the distal superficial femoral artery where challenging fatigue conditions are prevalent and stretched less in the mid and proximal superficial femoral artery where fatigue conditions are less challenging. In another example deployed implants 10, 20A, 20B and 20C are stretched more in the region of a previously deployed stent so as to minimize vessel stiffening in the already stiffened portion of the vessel and stretched less in the regions proximal to and distal to the previously deployed stent so as to provide adequate vessel scaffolding in the previously unstented region of the vessel. In other embodiments the implant when stretched will lengthen the majority of cells along the length of the implant. For example, each cell 18d, 18f of implants 20D and 20F tend to lengthen in similar amounts when the implant is stretched. In the case of stent implants, structures similar to implants 20D and 20F may be advantageous by maintaining a uniform percent metal coverage over the length of the stent.

In some embodiment's stretchable implant 10, 20A, 20B, 20C, 20D, or 20F offers advantages when comprised of biologically active drugs in the form of coatings, bound moieties, elutable molecules, or other forms over some or all of the implant. In one embodiment a uniformly coated implant is deployed with more implant structure (such as unstretched stent) in one region of the treatment site and less implant structure (such as stretched stent) in a second region of the treatment site, thereby allowing more drug to be delivered in the first region as compared to that delivered in the second region. In another embodiment a uniformly coated implant is deployed with more implant structure in one region of the treatment site and less implant structure in a second region of the treatment site, thereby allowing the structure in the second region to be driven more deeply into the treatment site as compared to the structure in the first region, allowing different kinetics of drug delivery in the two regions. In yet another embodiment, a stretchable implant can be comprised of drugs confined in a brittle coating that is cracked on stretching of the implant. Said coating can isolate reactive drugs from each other, can provide barrier functions for improved drug shelf life, can confine liquids, or have other functions. In one example a stretchable implant comprised of brittle coating is stretched prior to deployment over at least a portion of it's length to alter drug release kinetics from the coating. In another example a stretchable implant comprised of brittle coating is stretched over at least a portion of it's length prior to deployment to fracture reservoirs of two or more drugs that will react with one another so as to form a more desirable bioreactive species. In another example a stretchable implant comprised of brittle coating is stretched over at least a portion of its length prior to deployment to fracture reservoirs of two or more drugs that desirable are delivered simultaneously to a treatment site.

Figure 5A:
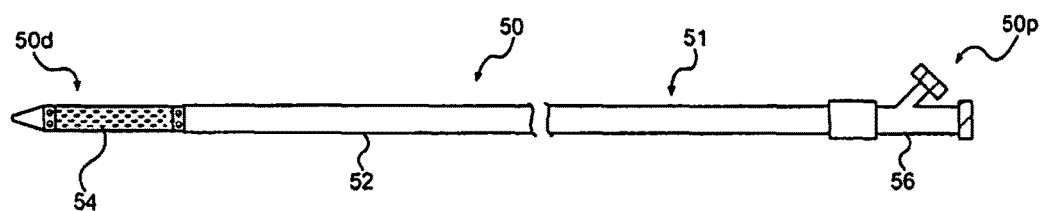
FIGS. 5A and 5B illustrate side elevation views of one embodiment of a stretchable implant system having features that are examples of inventive aspects in accordance with the principles of the present disclosure.
Figure 5B:
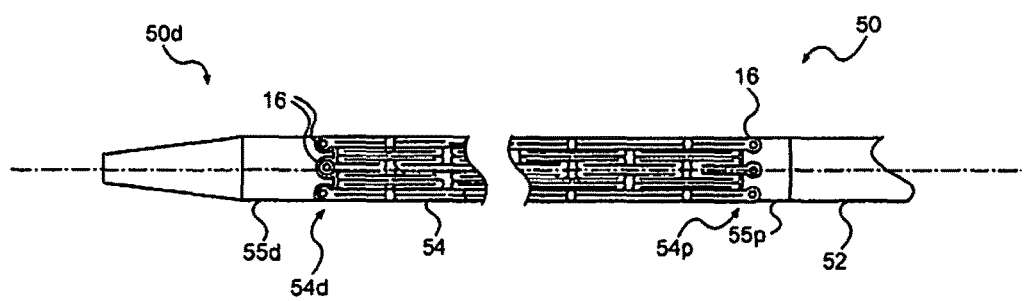
Figure 5C:
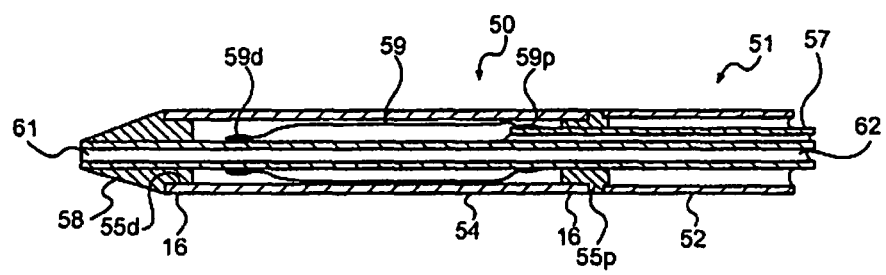
FIG. 5C illustrates a cross sectional view of the system of FIGS. 5A and 5B.
Figure 5D:
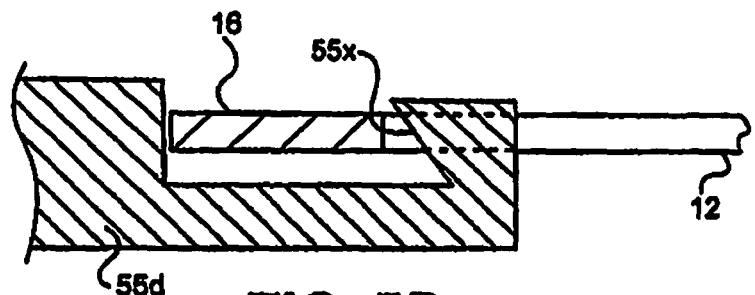
FIGS. 5D, 5E and 5F illustrate side elevation partial cross sectional views of a portion of the stretchable implant system illustrated in FIGS. 5A to 5C.
Figure 5E:
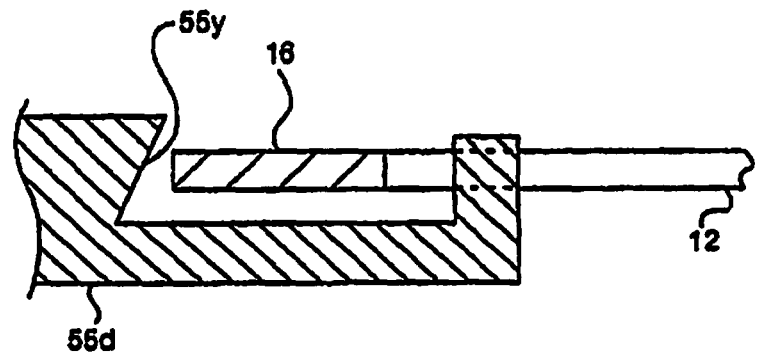
Figure 5F:
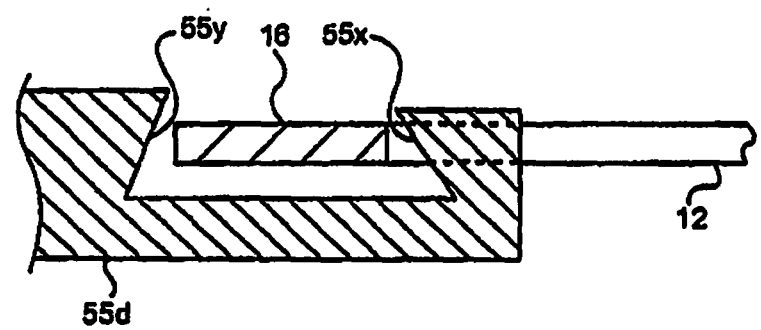

FIGS. 5A, 5B and 5C illustrate stretchable implant system 50 comprised of catheter 51 having stretchable stent 54 mounted on distal region 50d of catheter. Catheter 51 is comprised of catheter shaft 52, manifold 56, and retainers 55p and 55d. System 50 is configured to be advanced through the patient's body lumen. In use, system 50 is sufficiently long for distal region 50d to be placed at the deployment site in the patient's body lumen with proximal region 50p remaining external to the patient's body for manipulation by an operator. Working length of catheter 51, defined as the catheter length distal to manifold 56, is contemplated to be from 60 to 200 cm. Stretchable stent 54 has proximal end 54p, distal end 54d, is balloon expandable, and is secured to catheter 51 by crimping the stent to a delivery diameter onto balloon 59 with interlock of stent tabs 16 into pockets of retainers 55p and 55d. Stretchable stent 54 may be but is not limited to any of the stretchable stents 10, 20A, 20B, 20C, 20D, or 20F discussed previously and unstretched stent 54 lengths of from 20 mm to 400 mm are contemplated. Catheter shaft 52 is fixedly attached to proximal retainer 55p. Manifold 56 is attached to proximal region 50p of catheter shaft 52 and provides means for attachment of a stent expansion device and means for stretching stent 54. A guidewire channel (not shown in FIGS. 5A and 5B), extending from distal region 50d to proximal region 50p, is optionally provided in catheter shaft 52. FIG. 5C illustrates further that catheter 51 is comprised of bilumen inner member 57 having balloon inflation lumen 62, guidewire lumen 61, tip 58, distal retainer 55d, and having balloon 59 sealingly attached thereto at bonds 59p, 59d. Tip 58 and distal retainer 55d are fixedly attached to distal portion of bilumen inner member 57. Lumen 62 is in fluid communication with interior of balloon 59. Bilumen inner member 57 is slideable within catheter shaft 52 and attached retainer 55p Catheter shaft 52 of system 50 may have a variety of different constructions. Shaft 52 may have a tubular construction adapted to resist kinking, traverse through tortuous passageways, and to transmit axial and in some embodiments torsional forces along the length of the shaft. Shaft 52 may be constructed so as to have varying degrees of flexibility along its length, and may be comprised of nylon, PEBAX, polyester, Polyurethane, PVC, PEEK, liquid crystal polymer, polyimide, braid reinforcement, metal reinforcement, or other materials. In one embodiment, shaft 52 has a tubular construction of braid-reinforced polyester. Inner member 57 of system 50 is relatively flexible in bending, resists kinking, has high column stiffness and in some embodiments has high torsional stiffness. Inner member 57 may be comprised of nylon, PEBAX, polyester, PEEK, liquid crystal polymer, polyimide, braid reinforcement, metal reinforcement, or other materials. In one embodiment, inner member 57 has a bilumen tubular configuration, defining one lumen 61 that extends through an entire length of inner member 57 and one lumen 62 that extends through most of a length of inner member 57. This type of configuration allows the system to be passed over a guidewire for guiding the system to a desired implant deployment location and allows inflation of balloon 59. However, in other embodiments, inner member 57 can have a single lumen configuration that provides for balloon inflation only. Distal region 50d of system 50 includes a tapered and flexible distal tip 58 that is sufficiently flexible to permit advancement of stretchable implant system 50 through a patient's lumen while minimizing trauma to the walls of the patient's lumen. Tip 58 may be comprised of PEBAX, PVC silicone rubber, C-Flex, polyurethane, thermoplastic elastomer, polyfluoroethylene, hydrogenated (styrene-butadiene) copolymer, or other materials and may be connected to inner member 57 by bonding, overmolding, adhesives, or other means. Proximal facing edges of tip may be chamfered so as to reduce the possibility of snagging on an implant during proximal withdrawal of the tip through the implant. Balloon 59 is capable of expanding a balloon expandable stent at inflation pressures as high as 10, 14, 18, or 20 atmospheres and may be comprised of biaxially oriented polymers such as nylon, PEBAX, polyester, or other materials. Balloon 59 is sealingly attached to inner member 57 at bonds 59p and 59d using processes such as laser welding, heat bonding, adhesive bonding, or other processes as are known to those skilled in the art. Distal and proximal retainers 55d, 55p are attached to inner member 57 and shaft 52 respectively and have sufficient strength to stretch stent 54 without mechanical failure. Distal and proximal retainers 55d, 55p in the form of separate pieces can be secured to inner member 57, and proximal facing edges of distal retainer may be chamfered so as to reduce the possibility of snagging on an implant during proximal withdrawal of the retainer through the implant. Retainers 55d, 55p can be machined, etched, stamped, formed, injection molded from thermoplastics or metals, or otherwise fabricated into the surface of a ring of metal, engineering polymer, ceramic, or other material and the ring applied to inner member 57 and shaft 52 by adhesive bonding, welding, solvent welding, fusing, or other techniques known in the art. In some embodiments one or both of distal and proximal retainers 55d, 55p are formed as an integral/unitary structure with inner member 57 and shaft 52 respectively. In one embodiment one or both of retainers 55p, 55d are provided with inclined surface 55x that prevents tab 16 from exiting out of retainer when stent is tensioned along axis A (FIG. 5D). In another embodiment one or both of retainers 55p, 55d are provided with inclined surface 55y that prevents tab 16 from exiting out of retainer when stent is compressed along axis A (FIG. 5E). In yet another embodiment one or both of retainers 55p, 55d are provided with inclined surfaces 55x and 55y that prevent tab 16 from exiting out of retainer when stent is tensioned or compressed along axis A (FIG. 5F). Further, in some embodiments the minimum opening distance between inclined surfaces 55x and 55y is less than the corresponding dimension of tab 16 to prevent tab 16 from exiting out of retainer when stent is neither in tension nor in compression. In said embodiments stent is forced out of retainers 55d, 55p by the expanding force of balloon 59 against stent 54. Alternatively, pockets of retainers 55p, 55d can be filled with an adhesive or a space filling substance (not shown) to prevent exit of tab 16 from retainer 55d, 55p when stent is in tension, in compression, or in neither. Said substance may be comprised of polymers such as polyethylene, polyurethane, polybutylene, PEBAX, bioabsorbable polymers such as polyethylene oxide, Carbowax, malleable metals, or other materials.

Lumen 61 slideably receives a guidewire (not shown) and is dimensioned to allow low friction passage of a guidewire therewithin. Guidewires suitable for use with system 50 have a nominal outer diameter of 0.010", 0.012", 0.014", 0.018", 0.025", 0.035", 0.038", or other diameters. Catheter shaft 52 maximum outside diameter can range from about 3 Fr to about 10 Fr. A catheter shaft 52 outside diameter of about 5 Fr is desirable for compatibility with currently popular guide catheter (not shown) dimensions. In one embodiment catheter working length is about 145 cm.

Figure 6:
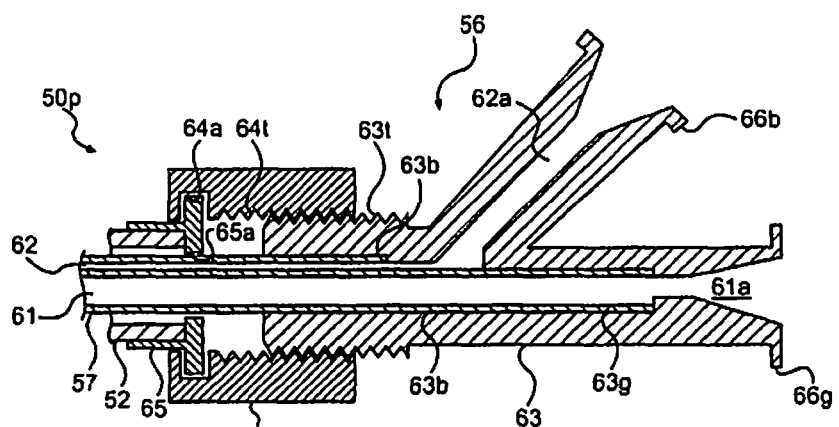
FIG. 6 illustrates an enlarged view of the proximal portion of the system of FIG. 5A.

FIG. 6 illustrates manifold 56 at proximal region 50p of stretchable implant system 50. Manifold 56 is comprised of Y-fitting 63, advancer 64, and flange 65. Outer surface of proximal most portion of inner member 57 is sealingly attached to inner wall 63g of Y-fitting 63 proximal to lumen 62a, and outer surface of inner member 57 is sealingly attached to inner wall 63b of Y-fitting 63 distal to lumen 62a. Lumen 62 of inner member 57 is in fluid communication with lumen 62a of Y-fitting 63 and lumen 61 of inner member 57 is in fluid communication with lumen 61a of Y-fitting 63. Y-fitting 63 is comprised of standard luer fittings 66b, 66g at proximal end of lumens 62a, 61a respectively. Shaft 52 is fixedly attached to flange 65, flange is held captive within groove 64a of advancer 64, flange is slideable within groove 64a and flange is slideable over inner member 57 by means of through hole 65a. In an alternate embodiment where length of stretchable stent is changed by applying torque to the stent, flange 65 is fixedly bonded to advancer 64. Advancer is slideably attached to Y-fitting 63 by means of threads 64t and 63t integral with advancer 64 and Y-fitting 63 respectively. Rotation of advancer 64 displaces catheter 52 relative to inner member 57, causing tensile or compressile forces to be transmitted through retainers 55p, 55d and tabs 16 to implant 54. In one embodiment manifold 56 is comprised of one or more indicators which display one or more of implant stretched, nominal, or compressed length.

Y-fitting 63, advancer 64, and flange 65 may be comprised of polycarbonate, polystyrene, or other materials. Alternate materials for these components are generally well known in the art can be substituted for any of the non-limiting examples listed above provided the functional requirements of the component are met. Inner member 57 may be sealingly attached to Y-fitting 63 using adhesives, welding, or other means as are known in the art. Catheter shaft 52 may be attached to flange 65 using adhesives, welding, or other means as are known in the art. Advancer/Y-fitting threaded connection is provided with sufficient axial travel to stretch and/or contract stent 54 over the entire design range of the stent. Optionally, a strain relief (not shown) may be attached to catheter shaft 52, flange 65, or both to prevent kinking of system 50 in the region proximate flange 65. Optionally, an access port and sealing means (not shown) may be provided on flange 65 so that fluid can be injected into the system to displace air from the annular space between inner member 57 and catheter shaft 52.

Figure 7C:
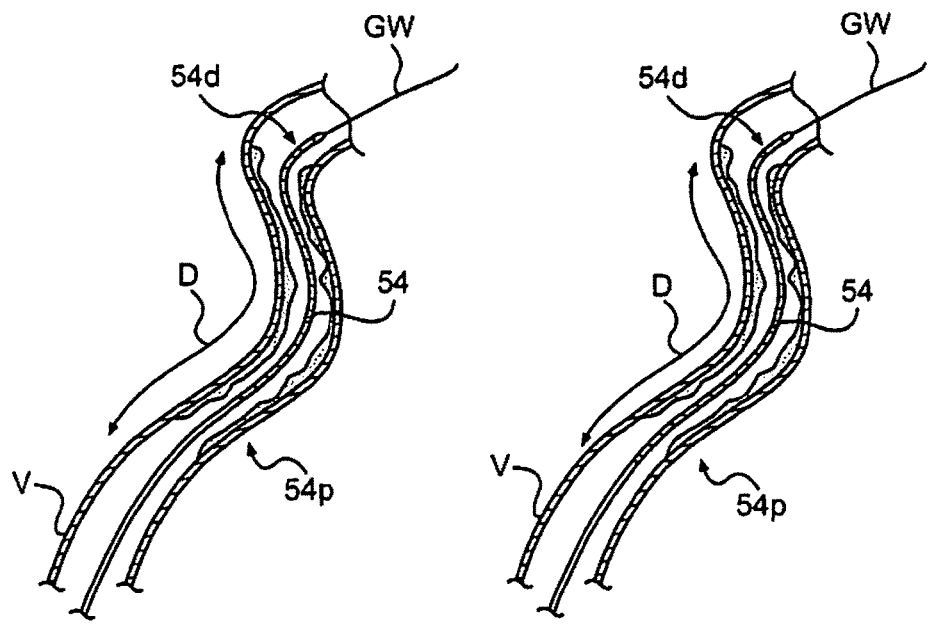
Figure 7C:
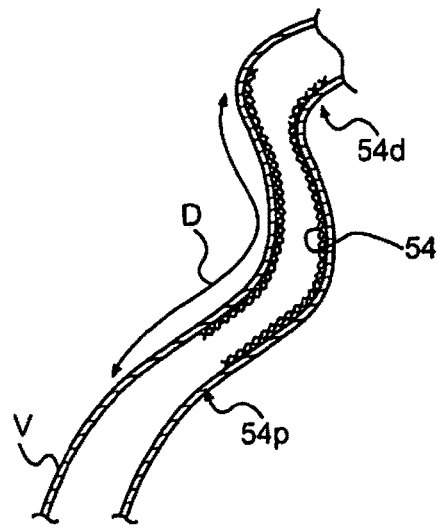

Exemplary methods of using stretchable implant system 50 in a body of a patient are now described with the assistance of FIGS. 7A, 7B and 7C. While a stent is chosen as the exemplary implant in the methods it is understood that the disclosure is not limited to stent implants.

Using techniques well known in the art, a guidewire GW is percutaneously inserted into a patient's blood vessel V and advanced to a region of interest in the patient's body. Using imaging techniques such as fluoroscopy the diseased portion D of the vessel is identified and a stretchable stent system comprised of a stretchable stent 54 having the correct length range and diameter range for treating the diseased portion D is chosen. Stretchable implant system 50 is advanced over the guidewire to the treatment site and by using imaging techniques such as fluoroscopy, markers 17 at distal end 54d of stent 54 are positioned at a correct location relative to the diseased portion D (FIG. 7A). Markers 17 at proximal end 54p of stent 54 are then imaged and by rotating advancer 64 stent 54 is stretched or contracted to the desired length as evidenced by positions of proximal and distal markers relative to disease length D (FIG. 7B).

Stretchable implant system 50 is held stationary, an inflation device (not shown) is attached to luer fitting 66b and used to inflate balloon 59. Inflated balloon expands stent 54 into contact with lumenal wall of vessel V, and balloon is then deflated using inflation device. Catheter 51 is repositioned such that balloon is within any unexpanded or underexpanded portion of stent 54, balloon is reinflated and subsequently deflated as many times as are needed to effect satisfactory stent contact with lumenal wall of vessel V. System 50 is then withdrawn from vessel V (FIG. 7C).

An alternative exemplary method of using a stretchable implant system 50 in a body of a patient is now described. Using techniques well known in the art, percutaneous access to a patient's blood vessel V is established. Using imaging techniques such as fluoroscopy the diseased portion of the vessel is identified and a stretchable stent system comprised of a stretchable stent 54 having the correct length range and diameter range for treating the diseased portion D is chosen. A guidewire is either back-loaded or front-loaded into lumen 61 of stretchable implant system 50 and the position of the guidewire is adjusted such that a short length (typically 10-20 cm) of the guidewire extends distally of tip 58. The system/guidewire combination is advanced through the patient's vessel to a region of interest in the patient's body. The combination is advanced to the treatment site and by using imaging techniques such as fluoroscopy markers 17 at distal end 54d of stent 54 are positioned at a correct location relative to the diseased portion D. Alternatively, the treatment site is initially crossed by further advancement of the guidewire alone, stretchable implant system 50 is subsequently advanced over the guidewire to the treatment site and by using imaging techniques such as fluoroscopy, markers 17 at distal end 54d of stent 54 are positioned at a correct location relative to the diseased portion D. Markers 17 at proximal end 54p of stent 54 are then imaged and by rotating advancer 64 stent 54 is stretched or contracted to the correct length as evidenced by positions of proximal and distal markers relative to disease length D.

Fitting/advancer of stretchable implant system 50 is held stationary, an inflation device is attached to luer fitting 66b and used to inflate balloon 59. Inflated balloon expands stent 54 into contact with lumenal wall of vessel V, and balloon is then deflated using inflation device. Catheter 51 is repositioned such that balloon is within any unexpanded or underexpanded portion of stent 54, balloon is reinflated, and subsequently deflated as many times as are needed to effect satisfactory stent contact with lumenal wall of vessel V. System 50 is then withdrawn from vessel V.

Figure 5G:
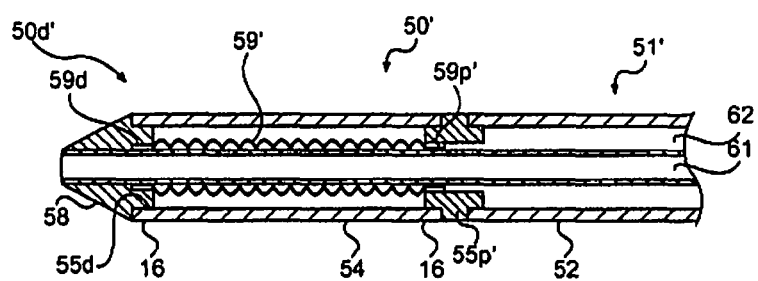
FIGS. 5G and 5H illustrate enlarged views of the distal and proximal portions, respectively, of an alternate embodiment of a stretchable implant system having features that are examples of inventive aspects in accordance with the principles of the present disclosure.
Figure 5H:
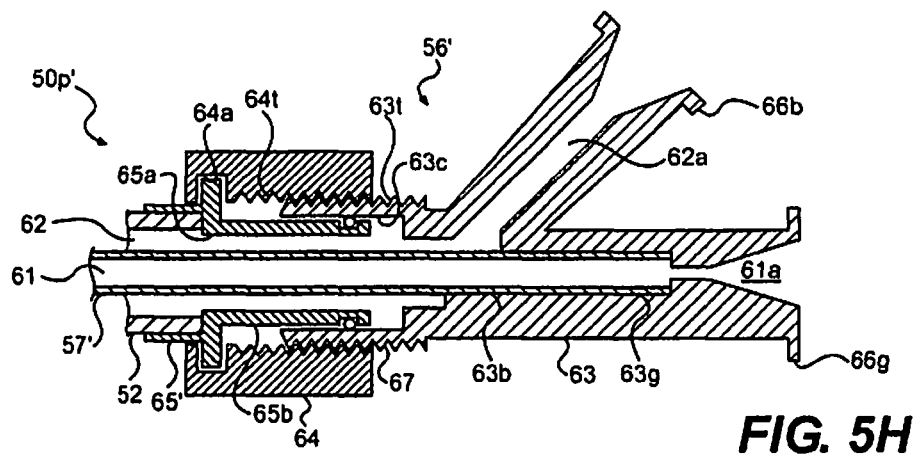

FIGS. 5G and 5H illustrate stretchable implant system 50', similar in many respects to stretchable implant system 50, and comprised of catheter 51' having stretchable stent 54 mounted on distal region 50d' of catheter. Catheter 51' is comprised of catheter shaft 52, manifold 56', and retainers 55p' and 55d. System 50' is configured to be advanced through the patient's body lumen. In use, system 50' is sufficiently long for distal region 50d' to be placed at the deployment site in the patient's body lumen with proximal region 50p' remaining external to the patient's body for manipulation by an operator. Working length of catheter 51', defined as the catheter length distal to manifold 56', is contemplated to be from 60 to 200 cm. Stretchable stent 54 has proximal end 54p, distal end 54d, is balloon expandable, and is secured to catheter 51' by crimping the stent to a delivery diameter onto balloon 59' with interlock of stent tabs 16 into pockets of retainers 55p' and 55d. Stretchable stent 54 may be but is not limited to any of the stretchable stents 10, 20A, 20B, 20C, 20D, or 20F discussed previously and unstretched stent 54 lengths of from 20 mm to 400 mm are contemplated. Catheter shaft 52 is fixedly attached to proximal retainer 55p' and corrugated balloon 59' is attached to proximal retainer 55p' at bond 59p'. Manifold 56' is attached to proximal region 50p' of catheter shaft 52 and provides means for attachment of a stent expansion device and means for stretching stent 54. A guidewire channel extending from distal region 50d' to proximal region 50p' is optionally provided in catheter shaft 52. Catheter 51' is comprised of single lumen inner member 57' having guidewire lumen 61, tip 58, distal retainer 55d, and having balloon 59' sealingly attached thereto at bond 59d. Balloon lumen 62 is formed by the annular space between the outer diameter of inner member 57' and the inner diameter of catheter shaft 52. Tip 58 and distal retainer 55d are fixedly attached to distal portion of inner member 57'. Lumen 62 is in fluid communication with interior of balloon 59'. Inner member 57' is slideable within catheter shaft 52 and attached retainer 55p'.

Retainer 55p', inner member 57', and bond 59p' have substantially the same construction, dimensions, and function as retainer 55p, inner member 57, and bond 59p respectively described above in conjunction with FIGS. 5A to 5C, as do all components having the same numbers in FIGS. 5A to 5C and 5G to 5H. Balloon 59' is capable of expanding a balloon expandable stent at inflation pressures as high as 10, 14, 18, or 20 atmospheres and has corrugations formed into the balloon during the balloon blowing process such that balloon is capable of stretching axially as stent is stretched prior to stent radial expansion. Balloon 59' may be comprised of biaxially oriented polymers such as nylon, PEBAX, polyester, polyurethane or other materials in monolithic or layered structures. Balloon 59 is sealingly attached to inner member 57 at bond 59d and to proximal retainer 55p at bond 59p using processes such as laser welding, heat bonding, adhesive bonding, or other processes as are known to those skilled in the art.

FIG. 5H illustrates manifold 56' at proximal region 50p' of stretchable implant system 50'. Manifold 56' is comprised of Y-fitting 63', advancer 64, and flange 65'. Outer surface of proximal most portion of inner member 57' is sealingly attached to inner wall 63g of Y-fitting 63 proximal to lumen 62a. Lumen 62 of catheter 51' is in fluid communication with lumen 62a of Y-fitting 63 and lumen 61 of inner member 57' is in fluid communication with lumen 61a of Y-fitting 63. Y-fitting 63 is comprised of standard luer fittings 66b, 66g at proximal end of lumens 62a, 61a respectively. Shaft 52 is fixedly attached to flange 65', flange is held captive within groove 64a of advancer 64, flange is slideable within groove 64a and flange is slideable over inner member 57 by means of through hole 65a. Flange 65' has proximal extension 65b with seal 67 housed in a groove in proximal extension 65b. Seal 67 creates a fluid tight axially slideable seal between exterior diameter of proximal extension 65b and inner diameter of counterbore 63c in Y-fitting 63. Advancer is slideably attached to Y-fitting 63 by means of threads 64t and 63t integral with advancer 64 and Y-fitting 63 respectively. Rotation of advancer 64 displaces catheter 52 relative to inner member 57', causing tensile or compressile forces to be transmitted through retainers 55p, 55d and tabs 16 to implant 54 and balloon 59'. In one embodiment manifold 56 is comprised of one or more indicators which display one or more of implant stretched, nominal, or compressed length.

Y-fitting 63', advancer 64, and flange 65' have substantially the same construction, dimensions, and function as Y-fitting 63, advancer 64, and flange 65 respectively described above in conjunction with FIGS. 5A to 5C. Optional strain relief, access port and sealing means, or both may be provided on flange 65' as described above in conjunction with FIG. 6. Seal 67 may be comprised of elastomeric materials such as butyl rubber, silicone rubber, Viton, C-flex, PVC, polyurethane, or other materials and may be molded, cut from sheet, or made using other processes known in the art.

Exemplary methods of using stretchable implant system 50' in a body of a patient are identical to those for stretchable implant system 50 with the following exceptions. When advancer 64 is rotated both the stent 54 and the balloon 59' will be stretched or contracted. Also, the initial balloon will expand substantially all of the length of the stretchable stent due to the length change of the balloon when the advancer is rotated. For this reason catheter 51' may not need to be repositioned to effect satisfactory stent contact with lumenal wall of vessel V.

Figure 8A:
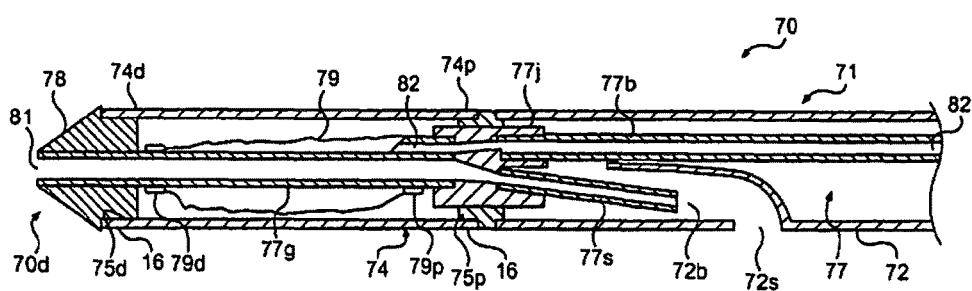
FIGS. 8A and 8B illustrate enlarged views of the distal and proximal portions, respectively, of an alternate embodiment of a stretchable implant system having features that are examples of inventive aspects in accordance with the principles of the present disclosure.
Figure 8B:
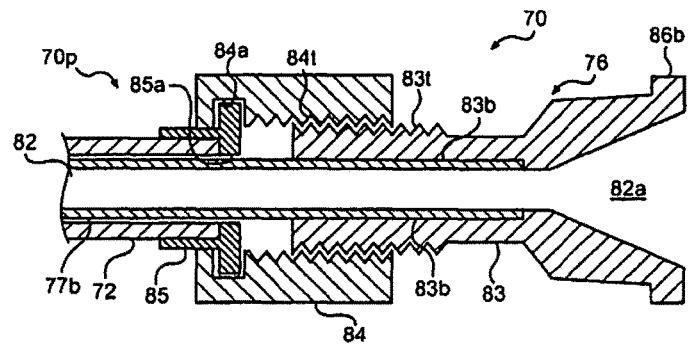

FIGS. 8A and 8B illustrate the distal and proximal ends respectively of an alternate embodiment of a stretchable implant system. Stretchable implant system 70 is comprised of catheter 71 having stretchable stent 74 mounted on distal region 70d of catheter. Catheter 71 is comprised of catheter shaft 72, proximal retainer 75p, and manifold 76. Working length of catheter, defined as the catheter length distal to manifold 76, is contemplated to be from 60 to 200 cm. Catheter 71 is further comprised of inner member 77 having single lumen proximal tube 77b, single lumen extension tube 77s, bilumen distal tube 77g having balloon inflation lumen 82, having guidewire lumen 81 and having balloon 79 sealingly attached thereto at bonds 79p and 79d, track 77j, tip 78, and distal retainer 75d. Tip 78 and distal retainer 75d are fixedly attached to distal tube 77g. Single lumen proximal tube 77b, single lumen extension tube 77s, and bilumen distal tube 77g are fixedly attached to track 77j. Lumen 82 is in fluid communication with interior of balloon 79. Proximal retainer 75p is slideable over track 77j and extension tube 77s is slideable within lumen 72b of bilumen distal portion of catheter shaft 72. Guidewire lumen 81 extends from distal region 70d of catheter to catheter port 72s. Stretchable stent 74 has proximal end 74p, distal end 74d, is balloon expandable, and is secured to catheter shaft 72 by crimping the stent to a delivery diameter onto balloon 79 with interlock of stent tabs 16 into pockets of retainers 75p and 75d. Stretchable stent 74 may be but is not limited to any of the stretchable stents 10, 20A, 20B, 20C, 20D, or 20F discussed previously and unstretched stent lengths of from 20 mm to 400 mm are contemplated. Manifold 76 is attached to proximal region 70p of catheter and provides means for attachment of a stent expansion device and means for stretching stent 74.

Catheter shaft 72, retainer 75p, inner member 77 (including tubes 77b, 77g, 77s and track 77j), lumen 81, balloon 79, bonds 79p and 79d, tip 78, and retainer 75d have substantially the same construction, dimensions, and function as catheter shaft 52, retainer 55p, inner member 57, lumen 61, balloon 59, bonds 59p and 59d, tip 58, and retainer 55d respectively described above in conjunction with FIGS. 5A to 5C. Track 77j may be comprised of polymers and may be manufactured using processes such as insert molding or reflow techniques.

FIG. 8B illustrates manifold 76 at proximal region 70p of stretchable implant system 70. Manifold 76 is comprised of fitting 83, advancer 84, and flange 85. Outer surface of proximal portion of tube 77b is sealingly attached to inner wall 83b of fitting 83. Lumen 82 of tube 77b is in fluid communication with lumen 82a of fitting 83. Fitting 83 is comprised of standard luer fitting 86b at proximal end of lumens 82a. Shaft 72 is fixedly attached to flange 85, flange is held captive within groove 84a of advancer 84, flange is slideable within groove 84a and flange is slideable over tube 77b by means of through hole 85a. In an alternate embodiment where length of stretchable stent is changed by applying torque to the stent, flange 85 is fixedly bonded to advancer 84. Advancer is slideably attached to fitting 83 by means of threads 84t and 83t integral with advancer 64 and fitting 83 respectively. Rotation of advancer 84 displaces shaft 72 relative to inner member 77, causing tensile or compressile forces to be transmitted through retainers 75p, 75d and tabs 16 to implant 74.

Fitting 83, advancer 84, and flange 85 have substantially the same construction, dimensions, and function as Y-fitting 63, advancer 64, and flange 65 respectively described above in conjunction with FIG. 6. Tube 77b and shaft 72 are attached to fitting 83 and flange 85 respectively in substantially the manner as inner member 57 and catheter 52 are attached to Y-fitting 63 and flange 65 respectively described above in conjunction with FIG. 6. Optional strain relief, access port and sealing means, or both may be provided on flange 85 as described above in conjunction with FIG. 6.

Exemplary methods of using stretchable implant system 70 are the same as the exemplary methods described above for using stretchable implant system 50.

Figure 9A:
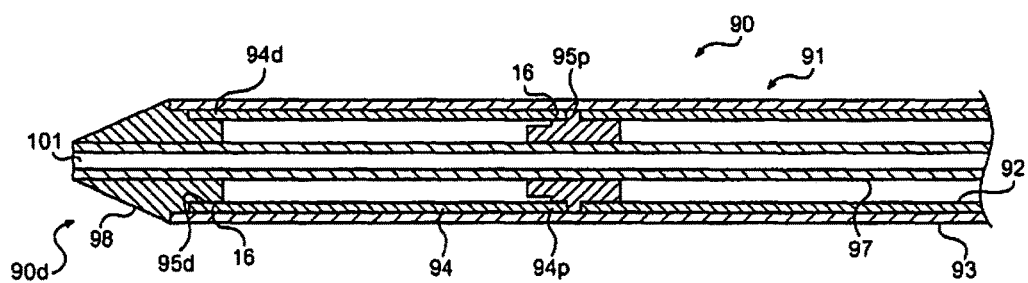
FIGS. 9A and 9B illustrate enlarged views of the distal and proximal portions, respectively, of an alternate embodiment of a stretchable implant system having features that are examples of inventive aspects in accordance with the principles of the present disclosure.
Figure 9B:
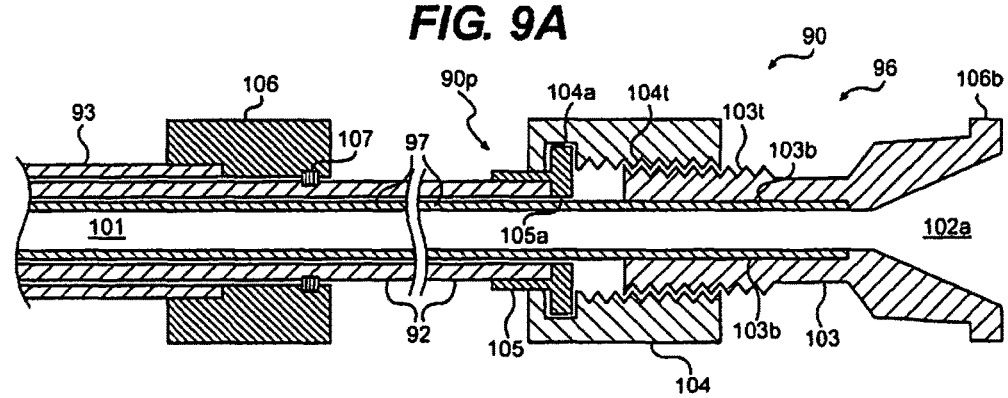
Figure 9C:
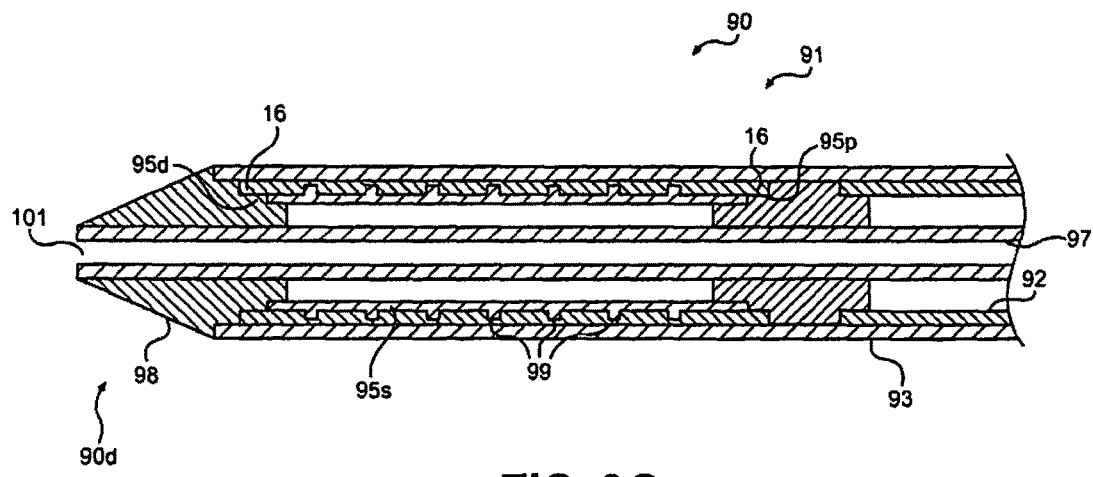
FIG. 9C illustrates a cross sectional view of a portion of the system of FIGS. 9A and 9B.

FIGS. 9A, 9B and 9C illustrate the distal and proximal portions respectively of an alternate embodiment of a stretchable implant system. Stretchable implant system 90 is comprised of catheter 91 having stretchable stent 94 mounted on distal region 90d of catheter. Catheter 91 is comprised of catheter shaft 92, retainer 95p, manifold 96 and sheath 93. Catheter shaft 92 is fixedly attached to retainer 95p. Working length of catheter 91, defined as the catheter length distal to handle 106, is contemplated to be from 60 to 200 cm. Catheter 91 is further comprised of inner member 97 having guidewire lumen 101, tip 98, and distal retainer 95d. Tip 98 and distal retainer 95d are fixedly attached to inner member 97. Retainer 95p is slideable over inner member 97 and sheath 93 is slideable over catheter shaft 92 and stent 94. Guidewire lumen 101 extends from distal region 90d of catheter to manifold 96. Stretchable stent 94 has proximal end 94p, distal end 94d, is self expandable, and is secured to catheter 91 by compressing the stent to a delivery diameter within sheath 93 with interlock of stent tabs 16 into pockets of retainers 95p and 95d. Stretchable stent 94 may be but is not limited to any of the stretchable stents 10, 20A, 20B, 20C, 20D, or 20F discussed previously and unstretched stent lengths of 20 mm to 400 mm are contemplated. Manifold 96 is attached to proximal region 90p of catheter, provides means for withdrawal of sheath 93 from stent 94, and provides means for stretching stent 94.

Catheter shaft 92, retainer 95p, inner member 97, lumen 101, tip 98, and retainer 95d have substantially the same construction, dimensions, and function as catheter shaft 52, retainer 55p, inner member 57, lumen 61, tip 58, and retainer 55d respectively described above in conjunction with FIGS. 5A to 5C. Sheath is fixedly attached to handle 106, has sufficient distal hoop strength to constrain self expanding stent 94 at a delivery diameter, has sufficient axial strength to be slid proximally off of stent 94 without damage or tensile failure, and sufficient flexibility to be advanced as part of system 90 through tortuous vessels. Sheath 93 may be comprised of polyester, nylon, PEEK, liquid crystal polymer, polyimide, metal reinforcement, or other materials and may be manufactured at least in part by extrusion, braiding, joining of tubing lengths, or other processes known in the art.

FIG. 9B illustrates manifold 96 at proximal region 90p of stretchable implant system 90. Manifold 96 is comprised of fitting 103, advancer 104, and flange 105. Outer surface of inner member 97 is sealingly attached to inner wall 103b of fitting 103. Lumen 101 of inner member 97 is in fluid communication with lumen 102a of fitting 103. Fitting 103 is comprised of standard luer fitting 106b at proximal end of lumen 102a. Shaft 92 is fixedly attached to flange 105, flange is held captive within groove 104a of advancer 104, flange is slideable within groove 104a and flange is slideable over inner member 97 by means of through hole 105a. In an alternate embodiment where length of stretchable stent is changed by applying torque to the stent, flange 105 is fixedly bonded to advancer 104. Advancer is slideably attached to fitting 103 by means of threads 104t and 103t integral with advancer 104 and fitting 103 respectively. Rotation of advancer 104 displaces shaft 92 relative to inner member 97, causing tensile or compressile forces to be transmitted through retainers 95p, 95d and tabs 16 to implant 94. Handle 106 houses seal 107 that is sealingly slideable over shaft 92. In a transport position, handle 106 and advancer 104 are spaced apart and sheath 93 covers stent 94 to prevent premature deployment of stent 94. When handle 106 and advancer 104 are moved toward each other, sheath 93 slides proximally relative to catheter 92 and inner member 97, uncovering self expanding stent 94, thereby permitting stent to deploy by radially expansion. Optionally, handle 106 may be provided with a lock (not shown) to limit axial movement of handle relative to catheter shaft 92 prior to deployment of stent 94.

Fitting 103, advancer 104, and flange 105 have substantially the same construction, dimensions, and function as Y-fitting 63, advancer 64, and flange 65 respectively described above in conjunction with FIG. 6. Handle 106 may be comprised of the same materials as fitting 103, advancer 104, or flange 105 and may comprise an annular groove along the inner diameter to house seal 107. Seal 107 may be comprised of elastomeric materials such as butyl rubber, silicone rubber, Viton, C-flex, or other materials and may be molded, cut from sheet, or made using other processes known in the art. Inner member 97 and shaft 92 are attached to fitting 103 and flange 105 respectively in substantially the manner as inner member 57 and catheter 52 are attached to Y-fitting 63 and flange 65 respectively described above in conjunction with FIG. 6. Optional strain relief, access port and sealing means, or both may be provided on flange 105 or handle 106 as described above in conjunction with FIG. 6.

Optionally, system 90 is comprised of stretchable stent retainer 95s as illustrated in FIG. 9C. Stretchable stent retainer influences stretching characteristics of stent 94. Stretchable stent retainer is fixedly attached to distal retainer 95d and proximal retainer 95p by molding, fusing, adhesive bonding, welding, or other means. Stretchable stent retainer is slideably attached to stent 94 by means of tabs 99. In some embodiments, tabs 99 protrude from surface of retainer 95s and into cells 18, 18a, 18b, 18c, 18d, or 18f of stents 10, 20A, 20B, 20C, 20D, or 20F respectively. Stretchable retainer 95s is axially stretches uniformly along its length, preferentially along one or more localized region along it's length, or at different rates along one or more localized region along it's length. Stretchable stent retainer may be comprised of polymers such as nylon, PEBAX, polyester, PEEK, of metals such as stainless steel, nitinol, or of other materials and may be fabricated using processes such as molding, extrusion, or other processes. In one embodiment retainer 95s is a coextruded tube comprised of nylon 12 tabs 99 and outer shell with a 72D PEBAX inner shell. Stretch rate of retainer 95s may be adjusted by varying the wall thickness of the retainer at various regions along the length of the retainer. In one embodiment retainer 95s has a uniform wall thickness over its length and undeployed stent 94/retainer 95s combination uniformly stretches along it's length prior to stent deployment. In another embodiment retainer 95s has a locally thin wall thickness over the distal and proximal thirds of its length and undeployed stent 94/retainer 95s combination preferentially stretches along the distal and proximal regions of retainer prior to stent deployment. In yet another embodiment retainer 95s has more one or more distinct regions of locally thin wall thickness over its length and undeployed stent 94/retainer 95s combination preferentially stretches at pre-programmed discrete regions along the length of the stent/retainer combination prior to stent deployment.

Exemplary methods of using stretchable implant system 90 in a body of a patient are now described. While a stent is chosen as the exemplary implant in the method it is understood that the disclosure is not limited to stent implants.

Using techniques well known in the art, a guidewire GW is percutaneously inserted into a patient's blood vessel V and advanced to a region of interest in the patient's body. Using imaging techniques such as fluoroscopy the diseased portion of the vessel is identified and a stretchable stent system comprised of a stretchable stent 94 having the correct length range and diameter range for treating the diseased portion is chosen. Stretchable implant system 90 is advanced over the guidewire to the treatment site and by using imaging techniques such as fluoroscopy markers 17 at distal end 94d of stent 94 are positioned at a correct location relative to the diseased portion. Markers 17 at proximal end 94p of stent 94 are then imaged and stent 94 is stretched or contracted to the correct length by rotating advancer 104 as evidenced by positions of proximal and distal markers relative to disease length.

Fitting/advancer of stretchable implant system 90 is held stationary and sheath 93 is withdrawn proximally to uncover stent 94 thereby permitting stent to deploy by radial self expansion. System 90 is then withdrawn from vessel.

In an alternative method, stretchable implant system 90 may be used according to the exemplary method described for using stretchable implant system 110.

Figure 10A:
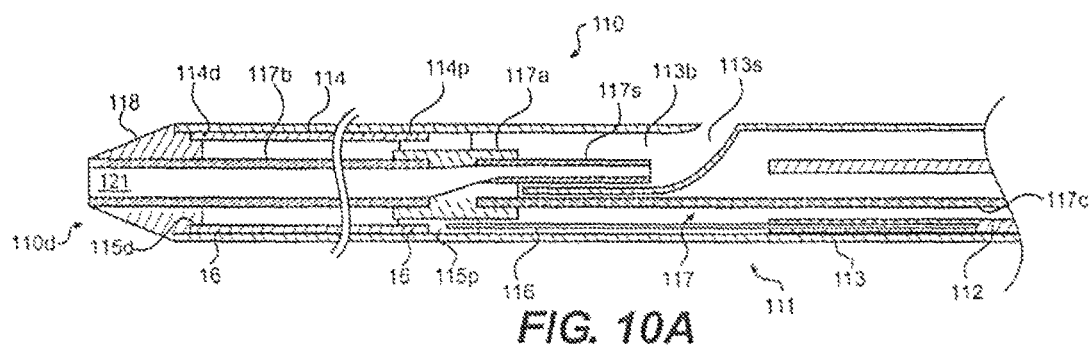
FIGS. 10A and 10B illustrate enlarged views of the distal and proximal portions, respectively, of an alternate embodiment of a stretchable implant system having features that are examples of inventive aspects in accordance with the principles of the present disclosure.
Figure 10B:
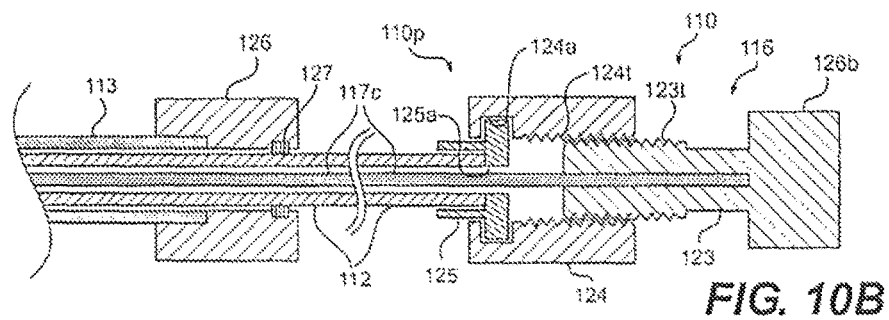

FIGS. 10A and 10B illustrate the distal and proximal portions respectively of an alternate embodiment of a stretchable implant system. Stretchable implant system 110 is comprised of catheter 111 having stretchable stent 114 mounted on distal region 110d of catheter. Catheter 111 is comprised of catheter shaft 112, extension rod 116, proximal retainer 115p, inner member 117, manifold 116 and sheath 113. Catheter shaft 112 is fixedly attached to extension rod 116 and extension rod 116 is fixedly attached to retainer 115p. The working length of catheter, defined as the catheter length distal to handle 126, is contemplated to be from 60 to 200 cm. Inner member 117 is further comprised of core rod 117c, track 117a, distal tube 117b, extension tube 117s, tip 118, and distal retainer 115d. Tip 118 and distal retainer 115d are fixedly attached to distal tube 117b, distal tube 117b is fixedly attached track 117a, and track 117a is fixedly attached to extension tube 117s and core rod 117c. Guidewire lumen 121 extends from distal region 110d of catheter to sheath port 113s. Sheath 113 is comprised of a single lumen over much of its length as well as a short bilumen portion in the vicinity of lumen 113b. Proximal retainer 115p is slideable over track 117a, single lumen extension tube 117s is slideable within lumen 113b of sheath 113, and sheath 113 is slideable over catheter shaft 112, retainer 115p and stent 114. Stretchable stent 114 has proximal end 114p, distal end 114d, is self expandable, and is secured to catheter 111 by compressing the stent to a delivery diameter within sheath 113 with interlock of stent tabs 16 into pockets of retainers 115p and 115d. Stretchable stent 114 may be but is not limited to any of the stretchable stents 10, 20A, 20B, 20C, 20D, or 20F discussed previously and unstretched stent lengths of 20 mm to 400 mm are contemplated. Manifold 116 is attached to proximal region 110p of catheter and provides means for withdrawal of sheath 113, thereby allowing stent self-expansion, and provides means for stretching stent 114. Optionally, a stretchable inner member (not shown) is fixedly attached to retainers 115p, 115d and slideably attached to stent 114 as described for stretchable implant system 90.

Catheter shaft 112, retainer 115p, lumen 121, tip 118, and retainer 115d have substantially the same construction, dimensions, and function as catheter shaft 52, retainer 55p, lumen 61, tip 58, and retainer 55d respectively described above in conjunction with FIGS. 5A to 5C. Distal tube 117b and extension tube 117s have substantially the same construction, dimensions, and function as inner member 57 described above in conjunction with FIGS. 5A to 5C. Sheath 113 has substantially the same construction, dimensions, and function as Sheath 93 described above in conjunction with FIGS. 9A to 9B. Track 117a may be comprised of polymers and may be manufactured using processes such as insert molding or reflow techniques. Extension rod 116 and core rod 117c may be comprised of metal, engineering polymer, or other materials intended to resist axial tensile and axial compressive deformation including but not limited to stainless steel, nitinol, liquid crystal polymer, PEEK, polyimide, metal reinforced materials, fiber reinforced materials, or other materials. Sheath is fixedly attached to handle 126, has sufficient distal hoop strength to constrain self expanding stent 114 at a delivery diameter, has sufficient axial strength to be slid proximally off of stent 114 without damage or tensile failure, sufficiently low coefficient of friction to allow for movement of the sheath across the compacted stent, and sufficient flexibility to be advanced as part of system 110 through tortuous vessels. Sheath 113 may be comprised of polyester, nylon, PEEK, liquid crystal polymer, polyimide, metal reinforcement, or other materials and may be manufactured at least in part by extrusion, braiding, or other processes known in the art.

FIG. 10B illustrates manifold 116 at proximal region 110p of stretchable implant system 110. Manifold 116 is comprised of fitting 123, advancer 124, and flange 125. Outer surface of core rod 117c is fixedly attached to fitting 123. Fitting 123 is comprised of handle 126b at proximal end of fitting 123. Shaft 112 is fixedly attached to flange 125, flange is held captive within groove 124a of advancer 124, flange is slideable within groove 124a and flange is slideable over core rod 117c by means of through hole 125a. In an alternate embodiment where length of stretchable stent is changed by applying torque to the stent, flange 125 is fixedly bonded to advancer 124. Advancer is slideably attached to fitting 123 by means of threads 124t and 123t integral with advancer 124 and fitting 123 respectively. Rotation of advancer 124 displaces shaft 112 relative to core rod 117c, causing tensile or compressile forces to be transmitted through retainers 115p, 115d and tabs 16 to implant 114. Handle 126 houses seal 127 that is sealingly slideable over shaft 112. In a transport position, handle 126 and advancer 124 are spaced apart and sheath 113 covers stent 114 to prevent premature deployment of stent 114. When handle 126 and advancer 124 are moved toward each other, sheath 113 slides proximally relative to catheter 112 and core rod 117c, uncovering self expanding stent 114, thereby permitting stent to deploy by radial expansion. Optionally, handle 126 may be provided with a user activated mechanical lock (not shown) to limit axial movement of handle relative to catheter shaft 112 prior to deployment of stent 114.

Fitting 123, advancer 124, and flange 125 have substantially the same construction, dimensions, and function as Y-fitting 63, advancer 64, and flange 65 respectively described above in conjunction with FIG. 6. Handle 126 may be comprised of the same materials as fitting 123, advancer 124, or flange 125 and may comprise an annular groove along the inner diameter to house seal 127. Seal 127 may be comprised of elastomeric materials such as butyl rubber, silicone rubber, Viton, C-flex, or other materials and may be molded, cut from sheet, or made using other processes known in the art. Core rod 117c and shaft 112 are attached to fitting 123 and flange 125 respectively in substantially the manner as inner member 57 and catheter 52 are attached to Y-fitting 63 and flange 65 respectively described above in conjunction with FIG. 6. Optional strain relief, access port and sealing means, or both may be provided on flange 125 or handle 126 as described above in conjunction with FIG. 6.

Exemplary methods of using stretchable implant system 110 in a body of a patient are now described. While a stent is chosen as the exemplary implant in the method it is understood that the disclosure is not limited to stent implants.

Using techniques well known in the art, percutaneous access to a patient's blood vessel V is established. Using imaging techniques such as fluoroscopy the diseased portion of the vessel is identified and a stretchable stent system comprised of a stretchable stent 114 having the correct length range and diameter range for treating the diseased portion is chosen. A guidewire is either back-loaded or front-loaded into lumen 121 of stretchable implant system 110 and the position of the guidewire is adjusted such that a short length (typically 10-20 cm) of the guidewire extends distally of tip 118. The system/guidewire combination is advanced through the patients vessel to a region of interest in the patient's body. The combination is advanced to the treatment site and by using imaging techniques such as fluoroscopy markers 17 at distal end 114d of stent 114 are positioned at a correct location relative to the diseased portion. Alternatively, the diseased portion is initially crossed by further advancement of the guidewire alone, stretchable implant system 110 is subsequently advanced over the guidewire to the treatment site and by using imaging techniques such as fluoroscopy markers 17 at distal end 114d of stent 114 are positioned at a correct location relative to the diseased portion. Markers 17 at proximal end 114p of stent 114 are then imaged and stent 114 is stretched or contracted to the correct length by rotating advancer 124 as evidenced by positions of proximal and distal markers relative to disease length.

Fitting/advancer of stretchable implant system 110 is held stationary and sheath 113 is withdrawn proximally to uncover stent 114 thereby permitting stent to deploy by radial self expansion. System 110 is then withdrawn from vessel.

In an alternative method, stretchable implant system 110 may be used according to the exemplary method described for using stretchable implant system 90.

In a further alternative method, stretchable implant system 50, 70, 90, 110 may be used advantageously during delivery of an implant through a tortuous path, for example, to a treatment site in the brain. While a stent is chosen as the exemplary implant in this method it is understood that the disclosure is not limited to stent implants. A stretchable implant system comprised of a stretchable stent of a length suitable for treatment of a diseased vessel is chosen. The stent is stretched before introduction of the system into the tortuous path so as to increase the bending flexibility of the system in the region of the unexpanded stent. For example, a stent similar to implant 20C, when stretched, will be more flexible than when in an unstretched state due to increases in gaps 23. The stretchable implant system is then advanced through tortuosity to the treatment site and the stent is axially contracted to the length suitable for treatment of the diseased vessel. The stent is then deployed and the system is withdrawn from the patient.

Figure 11:
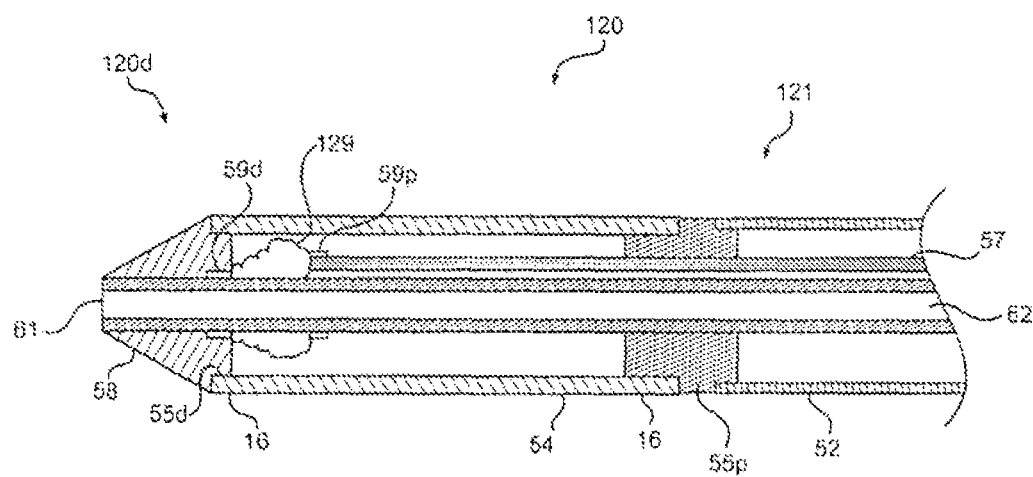
FIG. 11 illustrates an enlarged view of the distal portion of an alternate embodiment of a stretchable implant system having features that are examples of inventive aspects in accordance with the principles of the present disclosure.

FIG. 11 illustrates the distal portion of an alternate embodiment of a stretchable implant system. Stretchable implant system 120 is comprised of catheter 121 having stretchable stent 54 mounted on distal region 120d of catheter, short balloon 129 mounted on distal region of inner member 57, and manifold 56 (illustrated in FIG. 6). Aside from the shortened length of balloon 129 as compared to balloon 59, all components of system 120 have substantially the same construction, dimensions, and function as all components of system 50 described above in conjunction with FIGS. 5A to 5C and FIG. 6.

Figure 12A:
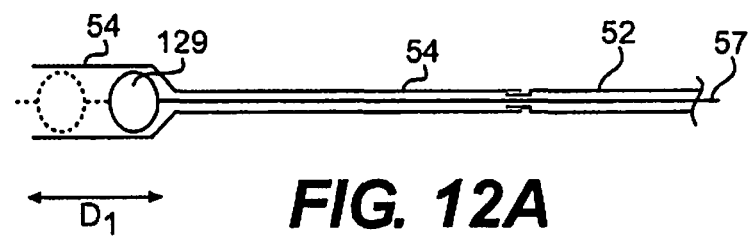
FIGS. 12A-C illustrate schematic views of the distal portion of the system of FIG. 11 in various states of implant deployment.
Figure 12B:
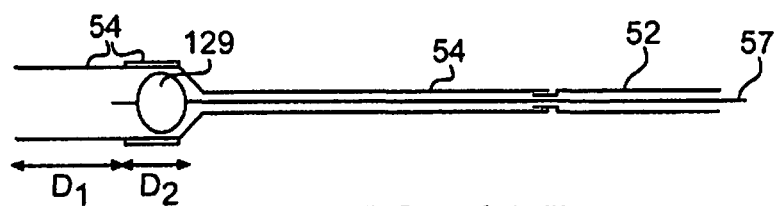
Figure 12C:
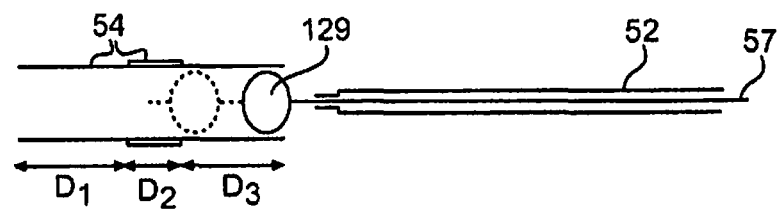

Exemplary methods of using stretchable implant system 120 in a body of a patient are now described with the assistance of schematic illustrations in FIGS. 12A to 12C. While a stent is chosen as the exemplary implant in the methods it is understood that the disclosure is not limited to stent implants.

Using techniques well known in the art, percutaneous access to a patient's blood vessel V is established. Using imaging techniques such as fluoroscopy the diseased portion of the vessel is identified and a stretchable stent system comprised of a stretchable stent 54 having the correct length range and diameter range for treating the diseased portion is chosen. A guidewire is either back-loaded or front-loaded into lumen 61 of stretchable implant system 120 and the position of the guidewire is adjusted such that a short length (typically 10-20 cm) of the guidewire extends distally of tip 58. The system/guidewire combination is advanced through the patients vessel to a region of interest in the patient's body. The combination is advanced to the treatment site and by using imaging techniques such as fluoroscopy markers 17 at distal end 54d of stent 54 are positioned at a correct location relative to the diseased portion. Alternatively, the diseased portion is initially crossed by further advancement of the guidewire alone, stretchable implant system 120 is subsequently advanced over the guidewire to the treatment site and by using imaging techniques such as fluoroscopy markers 17 at distal end 54d of stent 54 are positioned at a correct location relative to the diseased portion. If desired, stent 54 can be stretched by rotating advancer 64 prior to initial deployment. Distal end of stent 54 is then deployed by inflating balloon 129. Stent 54 is then stretched in-situ by pulling catheter 120 proximally so that stent 54 becomes tensioned between deployed segment (which is anchored to the vessel in an expanded form) and proximal retainer 55p. A stretched portion of stent 54 is then deployed over region D1 by adjusting position of balloon 129 relative to stent and then inflating balloon 129 (FIG. 12A, with one alternate balloon position shown in phantom). Stent 54 is then contracted in the vicinity of disease D2 and the contracted portion of stent 54 is then deployed by adjusting position of balloon 129 relative to stent and then inflating balloon 129 (FIG. 12B with contracted portion of stent shown by heavy line). Stent 54 is then again stretched in-situ and proximal most stretched portion of stent 54 is then deployed by adjusting position of balloon 129 relative to stent and inflating balloon 129 (FIG. 12C, with one alternate balloon position shown in phantom). System 110 is then withdrawn from vessel. Optionally, fully deployed stent 54 is further expanded using a balloon long enough to extend over the entire length of the expanded stent.

In an alternate exemplary method, May-Thurners syndrome is treated by deploying compressed stent 54 in the region of crushed vein and deploying stretched stent 54 in the region of un-crushed vein.

While the various embodiments of the present disclosure have related to stents and stent delivery systems, the scope of the present disclosure is not so limited. It will be appreciated that the various aspects of the present disclosure are also applicable to systems for delivering other types of expandable implants. By way of non-limiting example, other types of expanding implants include anastomosis devices, blood filters, grafts, vena cava filters, percutaneous valves, aneurism treatment devices, occlusion coils, or other devices.

It has been shown how the objects of the disclosure have been attained in a preferred manner. Modifications and equivalents of the disclosed concepts are intended to be included within the scope of the claims. Further, while choices for materials and configurations may have been described above with respect to certain embodiments, one of ordinary skill in the art will understand that the materials and configurations described are applicable across the embodiments.

What is claimed is:

1. An implant for insertion into a body lumen comprising:
an implant member including a plurality of cells at least partially defined by a plurality of struts and a plurality of bridges, selected of the cells disposed at proximal and distal ends of the implant and having terminal ends attached thereto, and the implant member having an initial length L1 extending along a longitudinal axis and an initial circumference C1 extending circumferentially about the longitudinal axis, wherein the implant member assumes a deformation circumference C2 having a value within 0% to 10% of a value of the initial circumference C1 following application of a deformation force substantially to the terminal ends thereof, wherein the deformation force substantially to the terminal ends results in the implant member assuming a permanent deformation length L2.

2. The implant of claim 1 wherein the deformation length L2 has a value between 3% to 50% greater than a value of the initial length L1.

3. The implant of claim 1, wherein the implant member is dimensioned to assume the deformation circumference C2 following application of the deformation force, the deformation force being substantially parallel to the longitudinal axis.

4. The implant of claim 1 wherein the deformation length L2 has a value between 10% to 50% greater than a value of the initial length L1.

5. The implant of claim 1 wherein the deformation circumference C2 has a value within 0% to 5% of a value for the initial circumference C1.

6. The implant of claim 1 wherein the implant member is a balloon-expandable stent.

7. The implant of claim 1 wherein two adjacent struts define a pair of struts, and wherein a first pair of struts is radially offset with respect to a second pair of struts, and wherein a bending region interconnects one strut from the first pair of struts and one strut from the second pair of struts.

8. The implant of claim 7 wherein a portion of the bending region is longitudinally aligned with a portion of at least one bridge.

9. The implant of claim 1 wherein a percentage of metal coverage of the implant at its initial length L1 is about 14%, and the percentage of metal coverage of the implant at its deformation length L2 is about 18%.

10. An implant for insertion into a body lumen comprising:
a tubular body extending for an initial length L1 along a longitudinal axis and having an initial circumference C1 about the longitudinal axis, the tubular body comprising a plurality of strut structures and a plurality of bridge structures collectively defining a plurality of cells, selected of the plurality of cells being disposed at proximal and distal ends of the tubular body and having terminal ends attached thereto, one of the plurality of strut structures and bridge structures being capable of deformation in a direction tending toward the longitudinal axis of the tubular body when a force substantially parallel to the longitudinal axis is applied to the terminal ends, wherein the application of one of tensile and compressive forces to the terminal ends results in the tubular body assuming a permanent deformation length L2 and a deformation circumference C2, and wherein the deformation circumference C2 has a value within 0% to 10% of a value for the initial circumference C1.

11. The implant of claim 10 wherein the deformation length L2 has a value between 3% to 50% greater than a value of the initial length L1.

12. The implant of claim 11 wherein the deformation length L2 has a value between about 10% to 50% greater than a value of the initial length L1.

13. The implant of claim 10 wherein the deformation length L2 has a value between about 20% to about 50% greater than a value of the initial length L1.

14. The implant of claim 10 wherein the deformation circumference C2 has a value within 0% to 5% of a value for the initial circumference C1.

15. The implant of claim 10 wherein the deformation circumference C2 has a value within 0% to 3% of a value for the initial circumference C1.

16. The implant of claim 10, wherein the circumference C2 is substantially equal to the circumference C1.

17. The implant of claim 10 wherein a yield force of the plurality of bridge structures normal to the longitudinal axis is less than a yield force of the plurality of strut structures normal to the longitudinal axis.

18. The implant of claim 10 wherein a yield force of the plurality of bridge structures normal to the longitudinal axis is less than a yield force of the terminal ends normal to the longitudinal axis.

19. The implant of claim 10 wherein a cross sectional area of the plurality of bridge structures normal to the longitudinal axis is less than a cross sectional area of the plurality of strut structures normal to the longitudinal axis.

20. The implant of claim 10 wherein a cross sectional area of the plurality of bridge structures normal to the longitudinal axis is less than a cross sectional area of the plurality of terminal ends normal to the longitudinal axis.

21. The implant of claim 10 wherein the tubular body is a stent.

22. The implant of claim 21 wherein the stent is self expandable.

23. The implant of claim 21 wherein the stent is balloon expandable.

24. The implant of claim 10 wherein two adjacent struts define a pair of struts, and wherein a first pair of struts is radially offset with respect to a second pair of struts, and wherein a bending region interconnects one strut from the first pair of struts and one strut from the second pair of struts.

25. The implant of claim 24 wherein a portion of the bending region is longitudinally aligned with a portion of at least one bridge.

26. The implant of claim 10 wherein a percentage of metal coverage of the implant at its initial length L1 is about 14%, and the percentage of metal coverage of the implant at its deformation length L2 is about 18%.

* * * * *